US009271920B2

(12) United States Patent
Wurm et al.

(10) Patent No.: US 9,271,920 B2
(45) Date of Patent: Mar. 1, 2016

(54) PVOH COPOLYMERS FOR PERSONAL CARE APPLICATIONS

(71) Applicant: Sekisui Specialty Chemicals America, LLC, Dallas, TX (US)

(72) Inventors: David Wurm, Houston, TX (US); Christa Grissom, Houston, TX (US); Richard Vicari, Houston, TX (US)

(73) Assignee: Sekisui Specialty Chemicals America, LLC, Dallas, TX (US)

( * ) Notice: Subject to any disclaimer, the term of this patent is extended or adjusted under 35 U.S.C. 154(b) by 118 days.

(21) Appl. No.: 14/103,449

(22) Filed: Dec. 11, 2013

(65) Prior Publication Data

US 2014/0163134 A1    Jun. 12, 2014

Related U.S. Application Data

(60) Provisional application No. 61/735,771, filed on Dec. 11, 2012.

(51) Int. Cl.
| | |
|---|---|
| *A61K 8/81* | (2006.01) |
| *A61Q 1/10* | (2006.01) |
| *A61Q 19/00* | (2006.01) |
| *A61Q 9/00* | (2006.01) |

(Continued)

(52) U.S. Cl.
CPC ............ *A61K 8/8129* (2013.01); *A61K 8/0212* (2013.01); *A61K 8/345* (2013.01); *A61K 8/817* (2013.01); *A61K 8/8158* (2013.01); *A61K 8/8182* (2013.01); *A61Q 1/10* (2013.01); *A61Q 9/00* (2013.01); *A61Q 19/00* (2013.01); *G06Q 30/0621* (2013.01); *A61K 2800/28* (2013.01); *A61K 2800/594* (2013.01)

(58) Field of Classification Search
CPC .................................................. A61K 8/8129
See application file for complete search history.

(56) References Cited

U.S. PATENT DOCUMENTS

| 3,677,990 A | 7/1972 | Barabas et al. |
| 4,283,384 A | 8/1981 | Jacquet et al. |

(Continued)

FOREIGN PATENT DOCUMENTS

| EP | 0140325 A2 | 5/1985 |
| EP | 0973490 A1 | 1/2000 |
| EP | 0978270 A1 | 2/2000 |

OTHER PUBLICATIONS

International Search Report and Written Opinion issued Mar. 27, 2014 in corresponding International application No. PCT/US2013/074431 (12 pages).

(Continued)

*Primary Examiner* — Michael Pepitone
(74) *Attorney, Agent, or Firm* — Osha • Liang LLP

(57) ABSTRACT

Epilatory compositions may be formed from: 40 to 80 wt % water; 5 to 30 wt % of a mixture of at least one polyvinyl alcohol and at least one polyvinyl alcohol copolymer; 1 to 15 wt % plasticizer, where the plasticizer is a linear or branched composition having from 3 to 15 wt % OH; and up to 40 wt % of one or more additives. Pore strip, keratonic plug removal, and other cosmetic applications may be formed from a similar composition, where the plasticizer is a linear, cyclic, or branched composition having greater than 25 wt % OH; and up to 40 wt % of one or more additives. The adhesive properties of the formulations may be tailored, where a low OH content may result in increased adhesion relative to plasticizers having a high OH content.

18 Claims, 12 Drawing Sheets

(51) Int. Cl.
  *G06Q 30/06*  (2012.01)
  *A61K 8/34*  (2006.01)
  *A61K 8/02*  (2006.01)

(56) References Cited

U.S. PATENT DOCUMENTS

| | | |
|---|---|---|
| 4,423,031 A | 12/1983 | Murui et al. |
| 5,013,543 A | 5/1991 | Mercado et al. |
| 5,512,277 A | 4/1996 | Uemura et al. |
| 5,939,093 A | 8/1999 | Park et al. |
| 5,985,300 A | 11/1999 | Crotty et al. |
| 6,159,493 A | 12/2000 | Chen et al. |
| 6,306,382 B1 | 10/2001 | Uemura et al. |
| 7,507,400 B2 | 3/2009 | Spina et al. |
| 8,444,707 B2 | 5/2013 | Acher et al. |
| 8,444,708 B2 | 5/2013 | Acher et al. |
| 2002/0037977 A1* | 3/2002 | Feldstein et al. ............... 526/60 |
| 2002/0110536 A1 | 8/2002 | Osumi et al. |
| 2003/0175333 A1 | 9/2003 | Shefer et al. |
| 2004/0161402 A1* | 8/2004 | Brooks et al. ............. 424/70.15 |
| 2005/0019291 A1 | 1/2005 | Zolotarsky et al. |
| 2006/0002878 A1 | 1/2006 | Acher et al. |
| 2006/0269489 A1 | 11/2006 | Adamy |
| 2009/0049619 A1 | 2/2009 | Moussouni et al. |
| 2009/0087499 A1 | 4/2009 | Ott, Jr. |
| 2012/0052035 A1 | 3/2012 | Ciemnolonski et al. |
| 2013/0022568 A1 | 1/2013 | Adamy et al. |
| 2013/0048004 A1 | 2/2013 | Wei et al. |
| 2013/0263388 A1 | 10/2013 | Acher et al. |

OTHER PUBLICATIONS

International Search Report and Written Opinion issued Sep. 12, 2014 in corresponding International application No. PCT/US2013/074429 (20 pages).
International Prelmiinary Report on Patentability issued Jun. 16, 2015 in corresponding International application No. PCT/US2013/074431 (8 pages).
International Prelmiinary Report on Patentability issued Jun. 16, 2015 in corresponding International application No. PCT/US2013/074429 (12 pages).
Final Office Action issued Dec. 7, 2015 in related U.S. Appl. No. 14/103,424 (10 pages).

* cited by examiner

PVOH COPOLYMERS FOR PERSONAL CARE APPLICATIONS

FIELD OF THE DISCLOSURE

Embodiments disclosed herein relate generally to cosmetic compositions useful in pore strips, epilatories, and other cosmetic applications.

BACKGROUND

Various compositions designed for providing treatment to or cleaning of the skin are commercially available, such as at supermarkets, cosmetic stores, and other locations. Treatment masks only very weakly adhere to the skin, such that the mask is easily removed, and are generally used for application and delivery of moisturizing agents and other beneficial agents to the skin through a wet, typically aqueous, environment. Removal masks are those designed to firmly adhere to the skin and thereby remove dirt, clogs, and excess corneum on the surface and in the pores of skin upon peeling off the mask.

Tactile properties of the masks may thus depend on the desired effect, such as treatment or exfoliation, for example. To complicate things further, end users have individualized preferences for how the mask feels when applied and/or adhered to the skin—some end users may prefer a soft feel, others may prefer a tighter feel, while some may prefer a stronger or weaker adhesion to the skin, among other concerns.

Compositions useful in pore strips and keratonic plug removers, are described in various publications, such as US2002/0110536, U.S. Pat. Nos. 5,512,277, 6,306,382, 6,159,493, US2013/0048004, and EP0969806.

Compositions useful in depilatories, which typically include a chemical for removing hair, are described in various publications, such as US2006/0002878, U.S. Pat. No. 7,507,400, US2009/0087499, US2012/0052035, US2013/0022568, EP2335676, EP1973517, EP1309308, EP2335676, EP0973490, and EP1973517.

Compositions useful in epilatories, used for physical removal of hair as opposed to the chemical removal in depilatories, are described in various publications, such as U.S. Pat. Nos. 8,444,707, 8,444,708, and US2013/0263388.

SUMMARY

In one aspect, embodiments disclosed herein relate to an epilatory composition. The composition may be formed from: 40 to 80 wt % water; 5 to 30 wt % of a mixture of at least one polyvinyl alcohol and at least one polyvinyl alcohol copolymer; 1 to 15 wt % plasticizer, wherein the plasticizer is a linear or branched composition having from 3 to 15 wt % OH; and up to 40 wt % of one or more additives.

In another aspect, embodiments disclosed herein relate to a composition useful in depilatory, pore strip, keratonic plug removal, and other cosmetic applications. The composition may be formed from 40 to 80 wt % water; 5 to 30 wt % of a mixture of at least one polyvinyl alcohol and at least one polyvinyl alcohol copolymer; 1 to 15 wt % plasticizer, wherein the plasticizer is a linear, cyclic, or branched composition having greater than 25 wt % OH; and up to 40 wt % of one or more additives.

Other aspects and advantages will be apparent from the following description and the appended claims.

DETAILED DESCRIPTION

Figure 1:
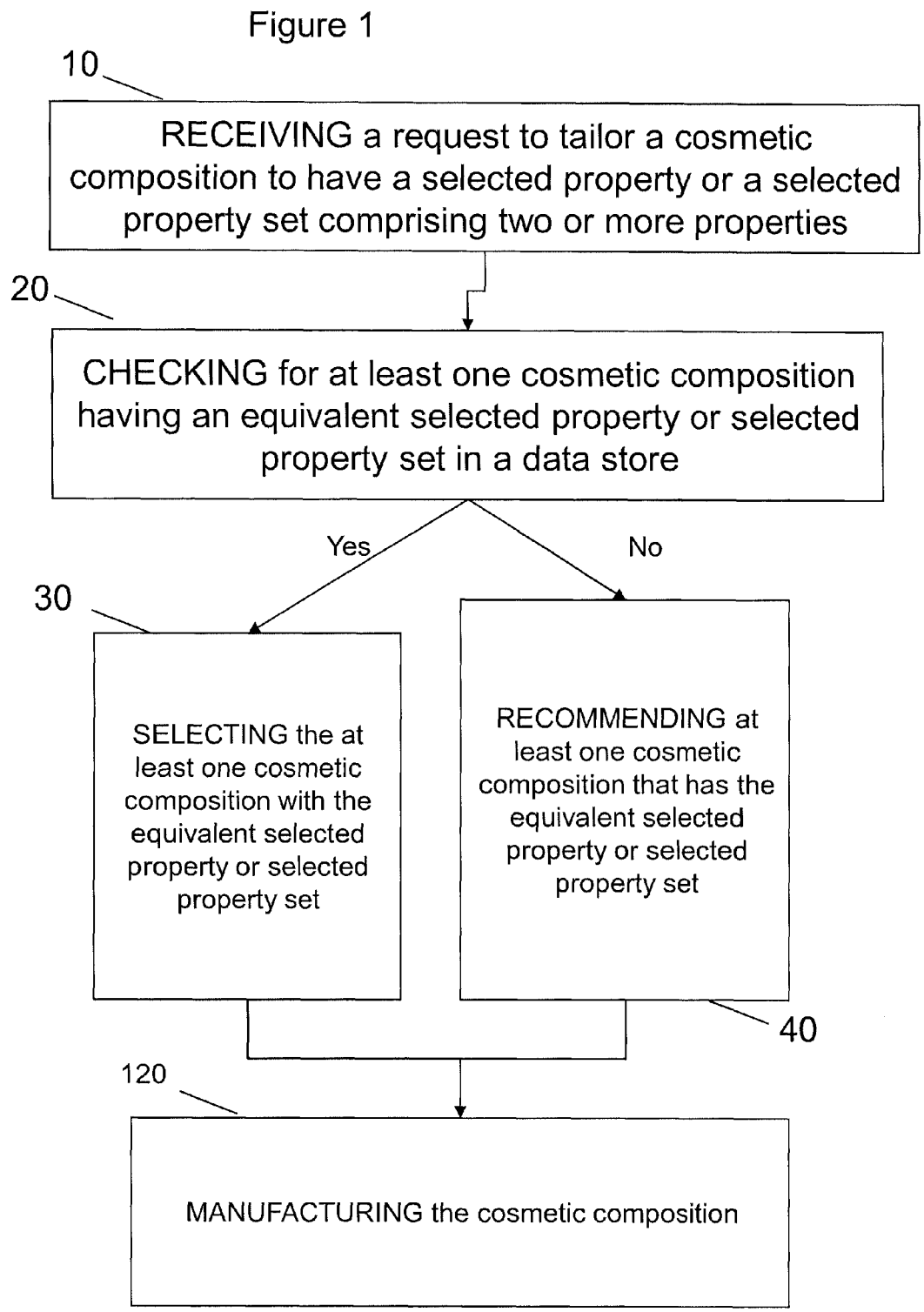
FIG. 1 is a simplified flow diagram of a method to prepare a cosmetic composition according to embodiments herein.

In one aspect, embodiments disclosed herein relate to cosmetic compositions useful in face masks, pore strips, keratonic plug removers, epilatories, and other cosmetic applications. In another aspect, embodiments disclosed herein relate to cosmetic compositions, where the cosmetic composition may provide a selected property, such as adhesion strength, softness, tensile strength, active delivery, or other various mechanical properties. In yet another aspect, embodiments disclosed herein relate to design or selection of a cosmetic composition to provide a selected mechanical property or combination of mechanical properties, i.e., a mechanical property set.

Cosmetic compositions according to embodiments herein may include water, at least one polyvinyl alcohol copolymer, and optionally one or more additives. For example, in some embodiments, cosmetic compositions according to embodiments herein may include: 40 to 80 weight percent water; 3 to 30 weight percent, such as 5 to 30 weight percent, of at least one polyvinyl alcohol copolymer; and up to 40 weight percent of one or more additives. In other embodiments, cosmetic compositions according to embodiments herein may include: 45 to 70 weight percent water; 10 to 20 or 10 to 30 weight percent of at least one polyvinyl alcohol copolymer; and up to 40 weight percent of one or more additives. In yet other embodiments, cosmetic compositions according to embodiments herein may include: 50 to 60 weight percent water; 12 to 15 weight percent of at least one polyvinyl alcohol copolymer; and up to 35 weight percent of one or more additives.

Any known process may be used to synthesize the polyvinyl alcohol copolymers, such as, but are not limited to, free radical polymerization, grafting, or redox initiation. For example, copolymers useful in embodiments herein may be formed by the copolymerization of a vinyl ester monomer and a comonomer via bulk polymerization, solution polymerization, emulsion polymerization, and suspension polymerization, among others. Vinyl esters monomers may include various aliphatic acids, such as vinyl formate, vinyl acetate, vinyl butyrate, vinyl pivalate, and vinyl versatate, among others, for example. The vinyl ester copolymer thus obtained may be saponified to form a vinyl alcohol copolymer. The resulting vinyl alcohol copolymer may have a degree of hydrolysis in the range from about 65 to about 99%, in some embodiments; in the range from about 75 to about 95% in other embodiments, as indicated by $C^{13}$NMR analyses.

The polyvinyl alcohol copolymers may have a number average molecular weight in the range from about 1000 to about 1000000 or more, such as in the range from about 10000 to about 300000. In other embodiments, the polyvinyl alcohol copolymers may have a degree of polymerization in the range from about 10 to about 25000 or more, such as in the range from about 500 to about 15000.

The polyvinyl alcohol copolymer may include up to 50% of at least one comonomer. Comonomers useful in embodiments herein may include amide comonomers, amine comonomers, pyrrolidone comonomers, and comonomers containing sulfonic acid groups, among others. In some embodiments, the comonomers may be incorporated into the polymer chain during polymerization of the vinyl ester, thus forming random vinyl alcohol copolymers.

Examples of pyrrolidone comonomers useful in embodiments herein may include compounds having a polymerizable carbon-carbon double bond and a pyrrolidone ring-containing group. Examples of the pyrrolidone ring-containing group include 2-oxopyrrolidin-1-yl, 3-propyl-2-oxopyrrolidin-1-yl, 5-methyl-2-oxopyrrolidin-1-yl, 5,5-dimethyl-2-oxopyrrolidin-1-yl, 3,5-dimethyl-2-oxopyrrolidin-1-yl, and the like. The carbon-carbon double bond contained in the pyrrolidone-ring-containing comonomer may include vinyl, allyl, styryl, acryloxy, methacryloxy, vinyloxy, allyloxyl, and other groups that are copolymerizable with the above noted vinyl esters of aliphatic acids and have a high alkali resistance at the time of copolymer hydrolysis to form the vinyl alcohol copolymer. Examples of the pyrrolidone-ring-containing comonomers may include N-vinyl-2-pyrrolidone, N-vinyl-3-propyl-2-pyrrolidone, N-vinyl-5-methyl-2-pyrrolidone, N-vinyl-5,5-dimethyl-2-pyrrolidone, N-vinyl-3,5-dimethyl-2-pyrrolidone, and N-allyl-2-pyrrolidone, among others.

Examples of amide comonomers useful in embodiments herein may include amide-group-containing monomers such as acrylamide, N,N-dimethyl acrylamide, N-methylolacrylamide, N-vinyl formamide, N-vinyl acetamide, and N-methyl-N-vinyl acetamide, among others.

Examples of the comonomers containing sulfonic acid groups may include vinyl sulfonic acid, allyl sulfonic acid, ethylene sulfonic acid, 2-acrylamido-1-methylpropanesulfonic acid, 2-acrylamido-2-methylpropanesulfonic acid, 2-methacrylamido-2-methylpropanesulfonic acid, 2-sulfoethyl acrylate, and salts thereof, among others.

Examples of other comonomers that may be used according to embodiments herein may include anionic monomers, e.g. monomers containing a carboxyl group(s) such as (meth)acrylic acid, maleic acid, maleic anhydride, fumaric acid, crotonic acid, itaconic acid, etc. and salts thereof; cationic monomers, e.g. monomers having a quaternary ammonium structure such as 3-(meth)acrylamido-propyl trimethyl ammonium chloride, etc; and nonionic monomers, e.g. alpha-olefins such as ethylene and propylene; (meth)acrylates such as methyl (meth)acrylate; alkyl vinyl ethers such as ethyl vinyl ether; silyl-group-containing monomers such as trimethoxy vinylsilane; hydroxyl-group-containing monomers such as allyl alcohol, dimethylallyl alcohol and isopropenyl alcohol; acetyl-group-containing monomers including allyl acetate, dimethylallyl acetate and isopropenyl acetate but excluding vinyl acetate; halogen-atom-containing monomers such as vinyl chloride, vinylidene chloride; amine containing monomers including vinylamine; and aromatic monomers such as styrene, among others.

The polyvinyl alcohol copolymer may include up to 50% of at least one of the above described comonomers, such as from a lower limit of about 0.5, 0.75, 1, 1.25, 1.5, 1.75, 2, 3, 4, or 5 weight percent to an upper limit of about 5, 10, 15, 20, or 25 weight percent, where any lower limit may be combined with any upper limit in various embodiments. In some embodiments, for example, the polyvinyl alcohol copolymer may include up to 20 weight percent N-vinyl pyrrolidone comonomer. In other embodiments, for example, the polyvinyl alcohol copolymer may include up to 10 weight percent 2-acrylamido-2-methylpropanesulfonic acid comonomer. In still other embodiments, for example, the polyvinyl alcohol copolymer may include up to 20 weight percent N-vinyl formamide comonomer.

Compositions disclosed herein may include a mixture of two or more of the above noted polyvinyl alcohol copolymers. Compositions disclosed herein may also include a mixture of one or more of the above noted polyvinyl alcohol copolymers with one or more polyvinyl alcohols. When used in admixture, the polymers may be used at any ratio, such as in the range from about 20:1 to 1:20, or in the range from about 1:10 to 10:1. The total amount of polyvinyl alcohol, when present, and polyvinyl alcohol copolymer may be in the range from about 3 to about 30 weight percent, such as from a lower limit of 5, 6, 7, 8, 9, or 10 wt % to an upper limit of 12, 15, 20, 25, or 30 wt %, where any lower limit may be combined with any upper limit. Polyvinyl alcohols useful in embodiments herein may be formed by the polymerization of one or more vinyl ester monomers via bulk polymerization, solution polymerization, emulsion polymerization, and suspension polymerization, among others. Vinyl esters monomers may include various aliphatic acids, such as vinyl formate, vinyl acetate, vinyl butyrate, vinyl pivalate, and vinyl versatate, among others, for example. The vinyl ester polymer thus obtained may be saponified to form a polyvinyl alcohol. The resulting polyvinyl alcohol may have a degree of hydrolysis in the range from about 65 to about 99%, in some embodiments; in the range from about 75 to about 95% in other embodiments, as indicated by $C^{13}$NMR analyses. The polyvinyl alcohol may have a number average molecular weight in the range from about 1000 to about 1000000 or more, such as in the range from about 10000 to about 300000. In other embodiments, the polyvinyl alcohol may have a degree of polymerization in the range from about 10 to about 25000 or more, such as in the range from about 500 to about 15000.

Additives useful in embodiments herein may include rheology modifiers, thickeners, surfactants, pigments, dispersions aids, moisture retention agents, waxes, oils, encapsulating agents, vitamins, active ingredients, proteins, preservatives, plasticizers, film formers, hydrating substances, silicones, UV filters and absorbers, alpha-hydroxy-acids, antioxidants, essential oils, emulsifiers and emulsion stabilizers, stability or performance additives, emulsifying agents, sensory modifiers, humectants, slip agents, solvents, gelling agents, fixatives, foam enhancers, deposition agents, hair protectants, opacifiers, pearlizers, plant extracts, polyquaterniums or combinations thereof, among others.

In some embodiments, the additives may include at least one of ethanol, propylene glycol, and glycerin. For example, a cosmetic composition according to embodiments herein may include 40-80 weight percent water, 5-30 weight percent polyvinyl alcohol random copolymer, such as a polyvinyl alcohol N-vinyl formamide copolymer, a polyvinyl alcohol N-vinyl amine copolymer, or a polyvinyl alcohol N-vinyl pyrrolidone copolymer, and up to about 40 weight percent of one or more additives, such as 10-25 weight percent ethanol, 3-5 weight percent of at least one of propylene glycol, glycerin, and polyethylene glycol, and optionally up to about 20 weight percent of other additives.

As another example, a cosmetic composition according to embodiments herein may include 40 to 80 weight percent water; 5 to 30 weight percent of a mixture of at least one polyvinyl alcohol and at least one polyvinyl alcohol copolymer; and up to 40 weight percent of one or more additives.

In certain embodiments, it has been found that the use of a mixture of a polyvinyl alcohol and a polyvinyl alcohol copolymer may result in the cosmetic composition exhibiting properties unexpected based on cosmetic compositions using the polymers individually. For example, it has been found that the adhesive properties of a film formed from a cosmetic composition including a mixture of a polyvinyl alcohol with a poly(vinyl alcohol)-co-(vinylamine) may be significantly greater than when either are used alone. In some embodiments, the enhanced adhesive properties of the mixture may be realized where a plasticizer, which is normally considered to decrease adhesive properties, is used, the plasticizer having from 3 to 15 wt % OH. For example, the plasticizer may include a polyethylene glycol having and OH content in the range from about 3, 4, 5, 6, or 7 wt % to about 10, 11, 12, 13, 14, or 15 wt %, where any lower limit may be combined with any upper limit. This synergistic effect may be advantageous for developing compositions having tailored properties.

The adhesive properties of a mixture with polyvinyl alcohol and the poly(vinyl alcohol)-co-(vinyl amine) copolymer may advantageously be used for epilatory compositions requiring a high degree of adhesion. For example, epilatory compositions may include 40 to 80 wt % water; 5 to 30 wt % of a mixture of at least one polyvinyl alcohol and at least one polyvinyl alcohol copolymer; 1 to 15 wt % plasticizer, where the plasticizer is a linear or branched composition having from 3 to 15 wt % OH; and up to 40 wt % of one or more additives. The selection of such a plasticizer may provide for the desired adhesive properties of the composition. The plasticizer may include a polyethylene glycol, the polyvinyl alcohol copolymer may include a vinyl alcohol-vinyl amine copolymer, which may have from greater than 0 to less than 20 wt % vinyl amine comonomer, such as 3 to 15 wt % vinylamine in some embodiments, and from 6 or 8 to 12 or 15 wt % vinylamine in yet other embodiments. In some embodiments, the composition may include from 10 to 25 wt % of a mixture of at least one polyvinyl alcohol and at least one polyvinyl alcohol copolymer. The epilatory composition may have a viscosity of greater than about 20000 cP, which may provide for drip-free application, a Brookfield yield value of at least 5, which may provide for extended shelf-life stability and ease of application/spreading, and an adhesion to glass of at least 500 g, providing sufficient strength for removal of the hair from the skin. Brookfield Yield value, as defined herein, is the apparent viscosity at 0.5 rpm minus apparent viscosity a 1 rpm divided by 100. In some embodiments, the composition may have an adhesion to glass in the range from about 500 or 600 to about 900 or 1000 g. The epilatory composition may have a drying time of less than 15 minutes in some embodiments; less than 10 minutes in other embodiments. In some embodiments, the composition, upon drying, may have a tensile strength to modulus ratio of at least 0.5; at least 0.6 in other embodiments; and may be characterized in that it is removable from skin in essentially one piece. "Essentially one piece," as used herein, refers to a film that is capable of being gradually removed in one peeling motion such that the majority of the film (e.g., 80%, 85%, 90% or more) is removed without requiring additional peeling. The epilatory composition may have a pH in the range from about 5.5 to about 7.5, such as from about 5.5 to 6.5, limiting the irritating effects of the composition, although slightly higher pH values, such as up to 8.5, may also be used.

The adhesive properties of a mixture with polyvinyl alcohol and the poly(vinyl alcohol)-co-(vinyl amine) copolymer may advantageously be used for depilatory, pore strip, keratonic plug removal, or other cosmetic compositions. For example, pore strip and keratonic plug removal compositions may include 40 to 80 wt % water; 5 to 30 wt % of a mixture of at least one polyvinyl alcohol and at least one polyvinyl alcohol copolymer; 1 to 15 wt % plasticizer, where the plasticizer is a linear, cyclic, or branched composition having greater than 25 wt % OH; and up to 40 wt % of one or more additives. The selection of such a plasticizer may provide for the desired adhesive properties of the composition. The plasticizer may include at least one of glycerin, propylene glycol, butylene glycol, and dextrose in some embodiments, and the polyvinyl alcohol copolymer may include a vinyl alcohol-vinyl amine copolymer, which may have from greater than 0 to less than 20 wt % vinyl amine comonomer, such as 3 to 15 wt % vinylamine in some embodiments, and from 8 to 15 wt % vinylamine in yet other embodiments. In some embodiments, the composition may include from 10 to 25 wt % of a mixture of at least one polyvinyl alcohol and at least one polyvinyl alcohol copolymer. The composition may have a viscosity of greater than about 20000 cP, which may provide for drip-free application, a Brookfield yield value of at least 5, which may provide for extended shelf-life stability and ease of application/spreading, and an adhesion to glass of at least 125 g, providing sufficient strength for treatment of the skin. In some embodiments, the composition may have an adhesion to glass in the range from about 175 to about 350 g. The composition may have a drying time of less than 15 minutes in some embodiments; less than 10 minutes in other embodiments. In some embodiments, the composition, upon drying, may have a tensile strength to modulus ratio of at least 0.5; at least 0.6 in other embodiments; and may be characterized in that it is removable from skin in essentially one piece. The composition may have a pH in the range from about 5.5 to about 7.5, such as from about 5.5 to about 6.5, limiting the irritating effects of the composition, although slightly higher pH values, such as up to 8.5, may also be used.

In some embodiments, a cosmetic composition according to embodiments herein may include 40 to 80 wt % water; 5 to 30 wt % of a mixture of at least one polyvinyl alcohol and at least one polyvinyl alcohol copolymer; and up to 40 wt % of one or more additives, where: the polyvinyl alcohol has a degree of polymerization in the range from about 900 to about 1500 and a degree of hydrolysis in the range from about 87 to about 89; and the polyvinyl alcohol copolymer comprises a copolymer of poly(vinyl alcohol)-copoly(vinylamine) having a degree of polymerization in the range from about 300 to about 600 and containing from about 3 mole % to about 15 mole % vinylamine, such as about 8 mole % to about 15 mole % vinylamine. In some embodiments, the polyvinyl alcohol and polyvinyl alcohol copolymer may be present in a weight ratio in the range from about 15:85 to about 65:35 (polyvinyl alcohol to polyvinyl alcohol copolymer), such as in the range from about 20:80 to 60:40 or in the range from about 25:75 to about 55:45.

In some embodiments, a cosmetic composition according to embodiments herein, which may be used as an eyeliner for example, may include a polyvinylpyrrolidone, a polyvinyl alcohol, a polyvinyl alcohol copolymer, such as a vinyl amine copolymer, water, and one or more additives. In some embodiments, the eyeliner composition may include 30 to 80 wt % water; 10 to 30 wt % of a mixture of a polyvinylpyrrolidone (15-25 wt %), at least one polyvinyl alcohol (1.5-7.5 wt %) and at least one polyvinyl alcohol copolymer (1.5-7.5 wt %); and up to 60 wt % of one or more additives, such as iron oxide, ethanol, propylene glycol, and others known to those skilled in the art of eyeliner formulation. The polyvinyl alcohol may have a degree of polymerization in the range from about 900 to about 1500 and a degree of hydrolysis in the range from about 87 to about 89. The polyvinyl alcohol copolymer may include a poly(vinyl alcohol)-copoly(vinylamine) having a degree of polymerization in the range from about 300 to about 600 and containing from about 3 mole % to about 15 mole % vinylamine. In some embodiments, the polyvinyl alcohol and polyvinyl alcohol copolymer may be present in a weight ratio in the range from about 15:85 to about 65:35 (polyvinyl alcohol to polyvinyl alcohol copolymer), such as in the range from about 20:80 to 60:40 or in the range from about 25:75 to about 55:45.

As another example, embodiments disclosed herein also relate to a cosmetic composition that may provide a soft feel, but may also be resilient enough so as to peel from the skin in essentially one piece. The composition may include 40 to 80 wt % water, 3 to 30 wt % of at least one polyvinyl alcohol random copolymer comprising up to 20 wt % of a pyrrolidone comonomer, and up to 40 wt % of one or more additives (inclusive of plasticizer, fragrances, preservatives, etc.). The cosmetic composition may have a modulus in the range from about 100 psi to about 500 psi, such as in the range from about 150 psi to about 350 psi. In some embodiments, the composition may have an elongation at break of at least 180%, at least 190%, or at least 200%.

In some embodiments, the soft but resilient cosmetic composition may have a tensile strength to modulus ratio of greater than about 0.7, such as greater than about 0.8, greater than about 0.9, greater than about 1.0, or greater than about 1.1 in various embodiments. The cosmetic composition may also include from about 3 to about 30 wt % of a polyvinyl alcohol used in admixture with the polyvinyl alcohol copolymer. When used in admixture, the polyvinyl alcohol and polyvinyl alcohol copolymer may be used in a weight ratio in the range from about 1:10 to about 10:1, such as in the range from about 1:5 to about 5:1 or in the range from about 1:3 to 3:1 or from about 1:2 to 2:1, including ratios of about 0.9:1 to 1.1:1 and 1:1. Such compositions may be characterized as having an adhesion to glass of at least 2 g, at least 10 g, at least 20 g, or at least 30 g in various embodiments, such as in the range from about 2 g to about 40 g, and may also be characterized in that they are removable from skin in essentially one piece.

The soft but resilient cosmetic compositions as described in these embodiments may provide the desired properties without having a greasy feel, such as may result from addition of excess amounts of plasticizer to achieve a similar soft feel; rather, the desired properties may be provided primarily by the polymer, copolymer, or mixture thereof without sacrificing other desirable qualities to achieve a similar soft feel. For example, the soft but resilient cosmetic compositions may include less than 10 wt % plasticizer in some embodiments; 8 wt % or less in other embodiments; 7 wt % or less in other embodiments; 6 wt % or less in other embodiments; 5 wt % or less in other embodiments; 4 wt % or less in other embodiments; and 3 wt % or less in yet other embodiments.

Some embodiments herein are also directed toward a drip-free composition (i.e., does not flow readily from the skin once applied) that may have an extended shelf-life (i.e., exhibiting no settling or separation over time). For example, compositions that are thick when standing, but thin when shear is applied may limit flow (dripping) after application and may be easily spreadable, thinning during application to the skin. The viscosity of compositions according to embodiments herein may be greater than 10,000 cP, greater than 20,000 cP, greater than 30,000 cP, or even greater than 40,000 cP. Brookfiel yield values, representative of shear thinning, may be greater than 5, greater than 50, greater than 75, or greater than 100 in various embodiments. A yield value greater than about 5 may provide for a substantially drip-free composition, and a yield value greater than about 20 is considered essentially drip-free in embodiments herein. In some embodiments, compositions herein may have a Brookfield yield value in the range from about 5 to 500, such as in the range from about 20 to about 400.

Cosmetic compositions according to embodiments herein may be manufactured by any process for forming a mixture comprising water, a polyvinyl alcohol copolymer, and one or more additives. For example, the cosmetic composition may be formed by mixing, blending, melt kneading, or other processes that may be used to dissolve or disperse the polyvinyl alcohol copolymer(s) and the one or more additives in an aqueous (including water or water/alcohol mixtures) base fluid.

The above described cosmetic compositions may be used for treating, cleaning, or conditioning human skin. For example, the above described cosmetic compositions may be used in face masks, such as a treatment mask or a removal mask, for cleansing, hair removal, dead skin removal, to deliver an active component, such as a medicinal active, a moisturizing active, a preventative active (such as a UV blocking agent), or others applications known in the art, or other end products that may be useful to treat, cleanse, or condition human skin.

The cosmetic compositions may be applied to human skin, such as by spreading the composition over an area to be treated, for example. The cosmetic composition may then be left in contact with the skin for a period of time, during which the cosmetic composition may: dry or solidify, forming a film or cake; deliver an active to the skin, such as a medicine, moisturizing agent, dye, or cleansing agent; adhere to the skin or hair in the contact area or adhere to dirt or other materials as may be contained in the pores of the skin in the contact area; or other desired end results or effect. After the desired end result or effect is achieved, the cosmetic composition may be removed from the human skin, such as by peeling, rubbing, scrubbing, rinsing, washing, and the like.

Epilatory compositions according to some embodiments herein may be applied to the skin, such as by spreading the composition over an area to be treated, for example. In other embodiments, the epilatory composition may be disposed on a substrate, such as adhered to a backing or film, forming a "patch" to be placed in contact with the skin, the backing providing a gripping surface for removal of the epilatory from the skin after drying.

Other compositions herein may also be used with a backing, such as pore strips and keratonic plug removers. However, cosmetic compositions herein may be useful for such treatments without the need for a backing, as they may be easily spreadable and may be removed from the skin in essentially one piece. Such embodiments may advantageously provide for enhanced contact of the cosmetic composition with the skin surface, as not limited by the backing, allowing the composition to readily conform to the facial features of an end user.

The comonomers useful in embodiments herein may provide for cosmetic compositions having a wide spectrum of properties, as described in the Examples below. For example, polyvinyl alcohol N-vinyl pyrrolidone copolymers according to embodiments herein may provide a softer film relative to a typical commercially available mask composition formed from polyvinyl alcohol. As another example, polyvinyl alcohol N-vinyl formamide copolymers according to embodiments herein may provide a mask having a high adhesion strength and/or a tighter feel as compared to a typical commercially available mask composition formed from polyvinyl alcohol. Other comonomers, mixtures of comonomers, or mixtures of polyvinyl alcohol copolymers may provide other varied effects on the properties of the resulting cosmetic compositions.

Embodiments disclosed herein also provide for a method of selecting or designing a cosmetic composition. As noted above, end users may have any number of preferences for how a cosmetic composition performs and how it interacts with the skin. For example, end users may focus on one or more properties of the end product when deciding whether or not to purchase or repeatedly purchase a particular cosmetic composition. There are several attributes that are important to the consumer for face masks, pore strips, and epilatories, including: 1) adhesion to the skin, 2) ability to remove the film or mask from the skin in essentially one piece, 3) relative tightness or looseness of the mask on the skin, 4) ease of washing the mask off, 5) compatibility with the skin surface (i.e., resulting in skin irritation or lack thereof); 6) ability to deliver active ingredients to the skin; 7) is fast drying (e.g., 15 minutes or less to dry); 8) having a non-greasy feel; 9) good spreading (must not be too viscous or too runny; and 10) ease and cleanliness (drip-free) of application to the skin.

The selection of comonomers and other composition variables, for example, may allow the tailoring of the cosmetic compositions to meet a desired target mechanical property or set of mechanical properties, such as feel, adhesive strength, peel properties, active delivery effectiveness, required drying times, ease of application and removal, as well as odor and color, among other factors. The ability to tailor the mechanical properties may also provide for meeting of extended shelf-life requirements (no settling or separation of the mixture), as well as drip-free application to the skin.

As an example of generating formulations to meet target properties, three different treatment areas include face masks, pore strips, and epilatories. Each of these compositions have different objectives, but may be formulated with similar base components, such as polyvinyl alcohols and polyvinyl alcohol copolymers. Embodiments herein may be used, for example, to tailor a composition to provide a desired adhesive strength, such as epilatories having an adhesion to glass value of greater than 400 g, pore strips, having an adhesion to glass value in the range from 125 g to about 350 g, and face masks, having an adhesion to glass value of less than 20 g.

The tailoring of compositions to the particular application provided by embodiments herein may also allow various improvements over prior art. For example, embodiments herein may provide for a drip-free face mask that: peels from the skin in essentially one piece, does not drip during application, but is easily spreadable, and is removable from the skin without pain, but strong enough to stay on the face. As another example, embodiments herein may provide for pore strips and keratonic plug removers that have adequate adhesion to remove keratonic plugs while minimizing pain, does not drip during application, but is easily spreadable, and conforms and clings to the face; such embodiments may eliminate the need for additional applicator or backing strips for such applications.

As yet another example, embodiments herein may provide for epilatories that peel in essentially one piece, have improved aesthetics, does not drip during application, but is easily spreadable at room temperature (no heating required), and conforms and clings to the face or other areas of the body. Such embodiments may be used without the need for an additional applicator or backing strips, however such may facilitate the removal of the film from the skin.

Referring now to FIG. 1, a flow diagram of a method for selecting, designing, or tailoring properties of a cosmetic composition according to embodiments disclosed herein is illustrated. In step 10, a request for a cosmetic composition having a selected property or a selected property set comprising two or more properties may be received. A data store may then be checked 20 for at least one cosmetic composition having an equivalent selected property or selected property set. The data store may include, for example, one or more computer-based files containing data associated with the polyvinyl alcohol polymers and copolymers, monomers and comonomers, additives, as well as resin compositions and cosmetic compositions containing the same. The data stored in the data store may include molecular weights, degree of polymerization, viscosity, physical and chemical properties, and other information as described below, among others.

When a cosmetic composition with the equivalent selected property or selected property set exists, the at least one cosmetic composition with the equivalent selected property or selected property set may be selected 30. When a cosmetic composition with the equivalent selected property or selected property set does not exist, at least one cosmetic composition that has the equivalent selected property or selected property set may be estimated or determined 40.

Estimating step 40 may include, for example, analyzing data in the data store, and recommending (i.e., to estimate or predict) at least one of a comonomer or mixture of comonomers for use in a polyvinyl alcohol copolymer, a comonomer content of the polyvinyl alcohol copolymer, a polyvinyl alcohol copolymer degree of polymerization, a polyvinyl alcohol copolymer degree of saponification, a water content, a polyvinyl alcohol copolymer content, a cosmetic composition additive, and a cosmetic composition additive content that may be used to provide the selected property or the selected property set of the cosmetic composition.

Figure 2:
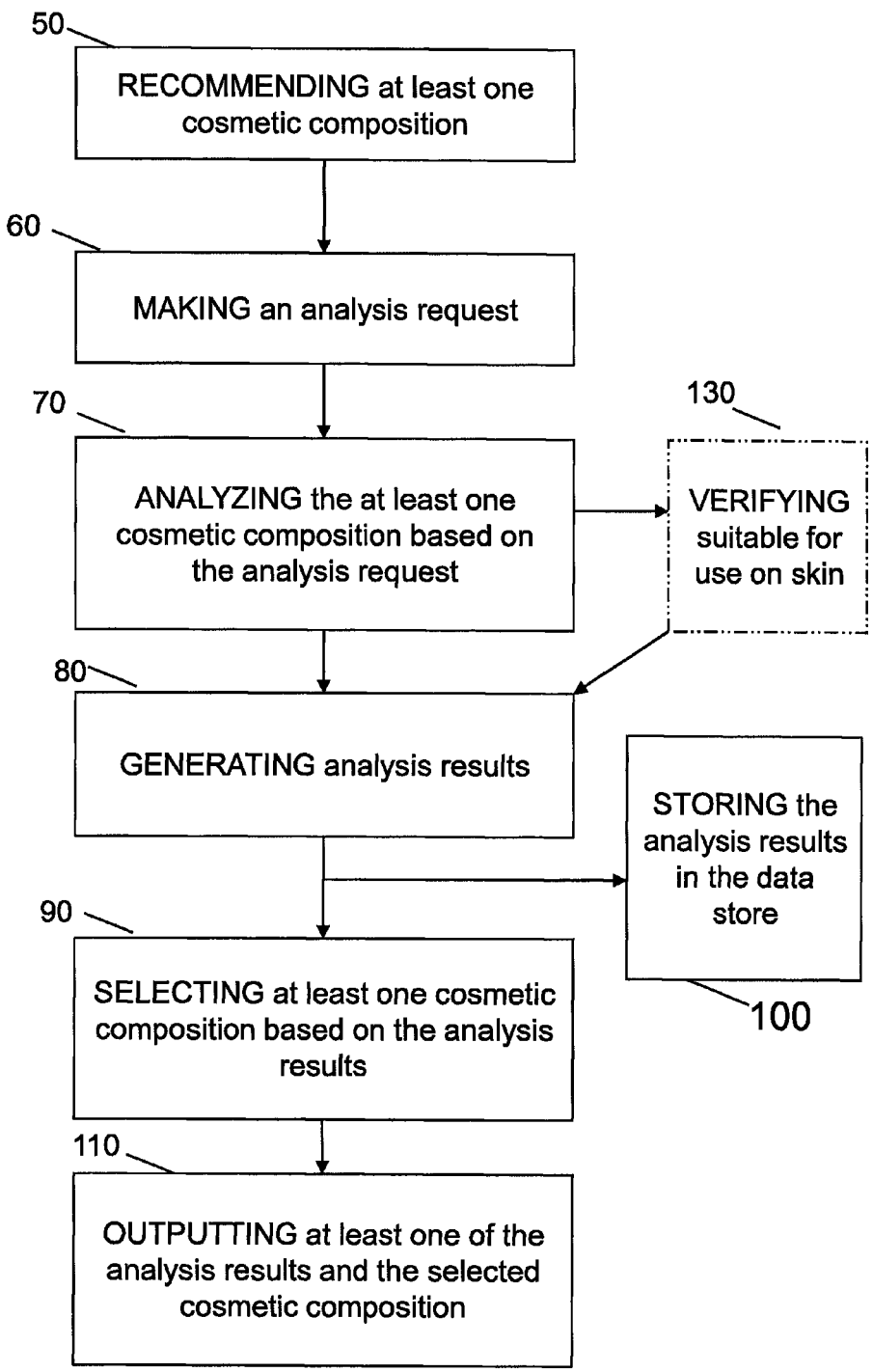
FIG. 2 is a simplified flow diagram of a method to prepare a cosmetic composition according to embodiments herein.

Referring now to FIG. 2, a flow diagram of one embodiment of recommending step 40 is illustrated, which may be a computer-aided method or simulation, for example. Estimating 40 may include, for example, recommending 50 at least one cosmetic composition; making an analysis request 60; analyzing 70 the at least one cosmetic composition based on the analysis request; generating 80 analysis results; and selecting 90 at least one cosmetic composition based on the analysis results. The method may also include storing 100 the analysis results in the data store.

The analysis request may include, for example, a request for at least one of tensile property analysis, adhesion analysis, texture analysis, active delivery analysis, and drying time analysis, among other analyses to quantify the mechanical properties of the composition. The analyzing may thus include, for example, determining at least one of a tensile property, adhesive property, texture property, and a drying property of at least one of a polyvinyl alcohol copolymer or mixtures thereof, a resin comprising a polyvinyl alcohol or polyvinyl alcohol copolymer, and a cosmetic composition comprising a polyvinyl alcohol or polyvinyl alcohol copolymer. Data may thus be accumulated relating monomers, comonomers, polyvinyl alcohol copolymer compositions, polyvinyl alcohol resins, and cosmetic compositions including the polyvinyl alcohol copolymers to the various properties analyzed, where such data may be added to and saved in the data store for future access and analyses. In some embodiments, the recommending 40 and/or analyzing 70 may further include verifying 130 that the recommended cosmetic composition is suitable for use on human skin; for example, ensuring that the adhesion force/peel strength is sufficiently low so as to not damage the skin upon removal of the film.

The recommending may include estimating or making an initial selection of at least one of a comonomer or mixture of comonomers for use in a polyvinyl alcohol copolymer, a comonomer content of the polyvinyl alcohol copolymer, a polyvinyl alcohol copolymer degree of polymerization, a polyvinyl alcohol copolymer degree of saponification, a cosmetic composition additive, and a cosmetic composition additive content to provide the selected property or the selected property set of the cosmetic composition.

The recommending 50, making 60, analyzing 70, and generating 80 based on the analysis results may then be repeated until a cosmetic composition meeting the selected property or the selected property set is designed. The analysis results and/or the cosmetic composition selected based on the estimating 40 may then be output 110, such as to a printer or a computer monitor, and a cosmetic composition based on the output or the estimating 40 may then be manufactured 120 to provide a customer the cosmetic composition having the selected property or selected property set.

EXAMPLES

Numerous simulated mask compositions were generated using different polyvinyl alcohols polymers and polyvinyl alcohol copolymers. The compositions may be regarded as "simulated" mask compositions, as additives such as fragrances and other minority components were not used. The polyvinyl alcohols and polyvinyl alcohols used include those described in Table 1. The simulated mask compositions and their properties are illustrated in Table 2.

TABLE 1

| Polymer | Description |
|---|---|
| Selvol™ Ultalux™ FA | A polyvinyl alcohol having a degree of polymerization of about 900-1500 and a degree of hydrolysis of about 87-89, available from Sekisui Specialty Chemicals, Dallas, Texas. |
| Selvol™ Ultalux™ FF | A polyvinyl alcohol having a degree of polymerization of about 1500-2500 and a degree of hydrolysis of about 87-89, available from Sekisui Specialty Chemicals, Dallas, Texas. |
| Selvol™ Ultalux™ FP | A polyvinyl alcohol having a degree of polymerization of about 300-600 and a degree of hydrolysis of about 87-89, available from Sekisui Specialty Chemicals, Dallas, Texas. |
| Selvol™ 107 | A polyvinyl alcohol having a degree of polymerization of about 350-700 and a degree of hydrolysis of about 98-99, available from Sekisui Specialty Chemicals, Dallas, Texas. |
| Selvol™ Ultalux™ AD | A copolymer of poly(vinyl alcohol)-copoly(vinylamine) having a degree of polymerization of about 300-600, the copolymer containing about 12 mole % of poly(vinylamine), available from Sekisui Specialty Chemicals, Dallas, Texas. |
| Ultalux™ M6i | A copolymer of polyv(vinyl alcohol)-co-poly(N-vinyl formamide) having a degree of polymerization of about 700-1500, the copolymer containing about 6 mole % N-vinyl formamide, available from Sekisui Specialty Chemicals, Dallas, Texas. |
| Vytek™ 2012 | A PVOH/AMPS copolymer that includes about 3.5 to 4 mol % AMPS and having a degree of hydrolysis of about 98%-99%, available from Celanese Chemicals, Dallas, Texas |
| Vytek™ 2025 | A PVOH/AMPS copolymer that includes about 3.5 to 4 mol % AMPS and having a degree of hydrolysis of about 98%-99%, available from Celanese Chemicals, Dallas, Texas |
| Selvol™ Ultalux™ SC | A PVOH/vinyl pyrrolidone copolymer having about 5 mol % vinyl pyrrolidone. |
| PVOH-co-PVP$_{10}$ | An experimental PVOH/vinyl pyrrolidone copolymer having about 10 mol % vinyl pyrrolidone. |

TABLE 1-continued

| Polymer | Description |
|---|---|

The polymer compositions were dissolved in deionized water (DI water) to form a base resin with no additives. This was accomplished by slowly adding the appropriate amount of polymer to unheated (<40° C.) DI water over a period of 3-5 minutes, while agitating in a mixing vessel. The solution was heated to 85° C., then held at this temperature for 30 minutes-2 hours, after which time the solution was allowed to cool to room temperature. Once at room temperature, additives were added to the base resin with mixing in order to form a "mask formulation." The solutions were then allowed to sit at room temperature until they became clear, indicating that the solutions were essentially free of air bubbles. Then Films from the resulting compositions were formed by casting the aqueous compositions onto a glass plate with a draw down bar film applicator (available from BYK Gardner, Columbia, Md.), and allowed to dry in a controlled temperature and humidity room with a constant temperature of 70° C. and humidity of 50% for a period of 12-24 hours. All films were thus conditioned before being characterized. A film target thickness of approximately 40 micrometers was achieved by using the appropriate draw-down bar. After conditioning in the controlled temperature and humidity room for a minimum of 12 hours, the resulting films are cut into test samples having an appropriate size for the desired test.

Viscosity properties of the solution were measured using a BROOKFIELD viscometer at 25° C., with spindle numbers 3-6, depending on the viscosity of the formulation. Since many of the formulations exhibit Non-Newtonian flow, viscosity is measured for at least three shear rates and reported at the theoretical zero shear rate. When reported with respect to Brookfield yield value (cP), the reported value is the apparent viscosity at 0.5 rpm minus the apparent viscosity at 1.0 rpm divided by 100.

Tensile properties of the resulting film were measured using an INSTRON Model 5542 (Norwood, Mass.). Water dissolution properties were measured by the method described below. A 600 mL beaker was filled with 500 mL of room temperature tap water. A magnetic stirrer was placed in the beaker and the beaker was placed on a stirrer platform, adjusting the vortex to be just over the 400 ml mark. The film was cut so that it fit securely inside a 35 mm by 23 mm POLAROID slide holder. The slide was then weighed with the sample in it and weight recorded. The slide was then placed in the holder and lowered into the vortex (5 mm away from the wall and 6 mm below water surface). As soon as the sample was submerged in the water, a stopwatch was started and the time when the film fully dissolved was recorded. This is referred to as the dissolution time.

Properties of the films formed from the resins and mask compositions measured included tensile properties and dissolution properties, presented in Table 2.

TABLE 2

| | Example Number | | | | | | | |
|---|---|---|---|---|---|---|---|---|
| Composition (% w/w) | 1 | 2 | 3 | 4 | 5 | 6 | 7 | 8 |
| Selvol™ Ultalux FA | 10 | | | | | | | |
| Selvol™ Ultalux FP | | 10 | | | | | | |
| Selvol™ 107 | | | 10 | | | | | |
| Selvol Ultalux™ AD | | | | 10 | | | | |
| Ultalux ™ M6i | | | | | 10 | | | |
| Vytek™ 2012 | | | | | | 10 | | |
| Vytek™ 2025 | | | | | | | 10 | |
| Selvol Ultalux SC | | | | | | | | 10 |

TABLE 2-continued

| PVOH-co-PVP$_{10}$ | | | | | | | | |
|---|---|---|---|---|---|---|---|---|
| DI Water | 60 | 60 | 60 | 60 | 60 | 60 | 60 | 60 |
| Ethanol | 20 | 20 | 20 | 20 | 20 | 20 | 20 | 20 |
| Propylene Glycol | 5 | 5 | 5 | 5 | 5 | 5 | 5 | 5 |
| Glycerin | 5 | 5 | 5 | 5 | 5 | 5 | 5 | 5 |
| Tensile Strength, psi | 996 | 532 | 682 | 422 | 1197 | 677 | 713 | 192 |
| Modulus, psi | 1197 | 2011 | 3145 | 1065 | 1722 | 566 | 714 | 162 |
| Elongation at Break, % | 199 | 148 | 132 | 189 | 198 | 197 | 185 | 200 |
| Dissolution, sec | 100 | 20 | >600 | 212 | 111 | 26 | 88 | 122 |

| | Example Number | | | | | | | |
|---|---|---|---|---|---|---|---|---|
| Composition (% w/w) | 9 | 10 | 11 | 12 | 13 | 14 | 15 | 16 |
| Selvol ™ Ultalux FA | | 5 | 5 | 5 | 12 | 12 | 12 | 12 |
| Selvol ™ Ultalux FP | | 5 | | | | | | |
| Selvol ™ 107 | | | | | | | | |
| Ultalux AD | | | 5 | | | | | |
| Ultalux ™ M6i | | | | | | | | |
| Vytek ™ 2012 | | | | | | | | |
| Vytek ™ 2025 | | | | | | | | |
| Selvol Ultalux SC | | | | | | | | |
| PVOH-co-PVP$_{10}$ | 6 | | | 5 | | | | |
| DI Water | 67 | 60 | 60 | 60 | 71 | 71 | 72 | 66 |
| Ethanol | 12 | 20 | 20 | 20 | 12 | 12 | 12 | 15 |
| Propylene Glycol | 9 | 5 | 5 | 5 | 5 | | 1 | 3 |
| Glycerin | | 5 | 5 | 5 | | 5 | 3 | 3 |
| Ascorbic Acid | | | | | | | | 1 |
| Tensile Strength, psi | 748 | 733 | 832 | 444 | 1900 | 1622 | 1762 | 1581 |
| Modulus, psi | 633 | 1850 | 1375 | 333 | 2721 | 2065 | 2285 | 2013 |
| Elongation at Break, % | >200 | 191 | 180 | 191 | 198 | >200 | >200 | 200 |
| Dissolution, sec | 66 | 111 | >600 | 11 | 92 | 92 | 92 | 100 |

| | Example Number | | | | | | | |
|---|---|---|---|---|---|---|---|---|
| Composition (% w/w) | 17 | 18 | 19 | 20 | 21 | 22 | 23 | 24 |
| Selvol ™ Ultalux FA | 15 | | 7.5 | 11.25 | 3.75 | 9 | 6 | 10 |
| Selvol ™ Ultalux FP | | | | | | | | |
| Selvol ™ 107 | | | | | | | | |
| Ultalux AD | | 15 | 7.5 | 3.75 | 11.25 | 6 | 9 | 5 |
| Ultalux ™ M6i | | | | | | | | |
| Vytek ™ 2012 | | | | | | | | |
| Vytek ™ 2025 | | | | | | | | |
| Selvol Ultalux SC | | | | | | | | |
| PVOH-co-PVP$_{10}$ | | | | | | | | |
| DI Water | 67 | 67 | 67 | 67 | 67 | 67 | 67 | 67 |
| Ethanol | 15 | 15 | 15 | 15 | 15 | 15 | 15 | 15 |
| Propylene Glycol | | | | | | | | |
| Glycerin | 3 | 3 | 3 | 3 | 3 | 3 | 3 | 3 |
| Ascorbic Acid | | | | | | | | |
| Adhesion to Glass, g | 72 | 249 | 490 | 320 | 256 | 360 | 420 | 370 |

There are several attributes that are important to the consumer for face masks, pore strips, and epilatories, as noted above, including: 1) adhesion to the skin, 2) ability to remove the film or mask from the skin in essentially one piece, 3) relative tightness or looseness of the mask on the skin, 4) ease of washing the mask off, 5) compatibility with the skin surface (i.e., resulting in skin irritation or lack thereof); 6) ability to deliver active ingredients to the skin; 7) quick drying (e.g., 15 minutes or less to dry); 8) has a non-greasy feel, 9) good spreading (must spread easily and evenly without being runny or feeling tacky and difficult to spread, where, in general, formulations having a viscosity in the range from about 4000 cSt to about 12000 cSt may be considered good spreading), and 10) ease and cleanliness (drip-free) of application to the skin. As shown by the properties of the examples in Table 1, embodiments disclosed herein may be used to predictably control all of these attributes by varying the PVOH and PVOH copolymers used in the formulation. For example, Examples 4 and 11 illustrate improved adhesion by employing a PVOH-vinyl amine copolymer in the formulation. The PVOH-co-vinylpyrrolidone containing formulations, examples 8, 9, and 12, have lower modulus (a proxy for how soft the mask is) than is achieved with other grades of PVOH and also show quicker dissolution times (a proxy for ease of removal). The VYTEK™ (sulfonate) copolymers also show quicker dissolution times than PVOH homopolymers. Furthermore, Example 11 illustrates an unexpected "synergistic" adhesion effect when a resin consisting of a blend of PVOH homopolymer and a PVOH-co-vinylamine is used to make a face mask formulation.

Figure 3:
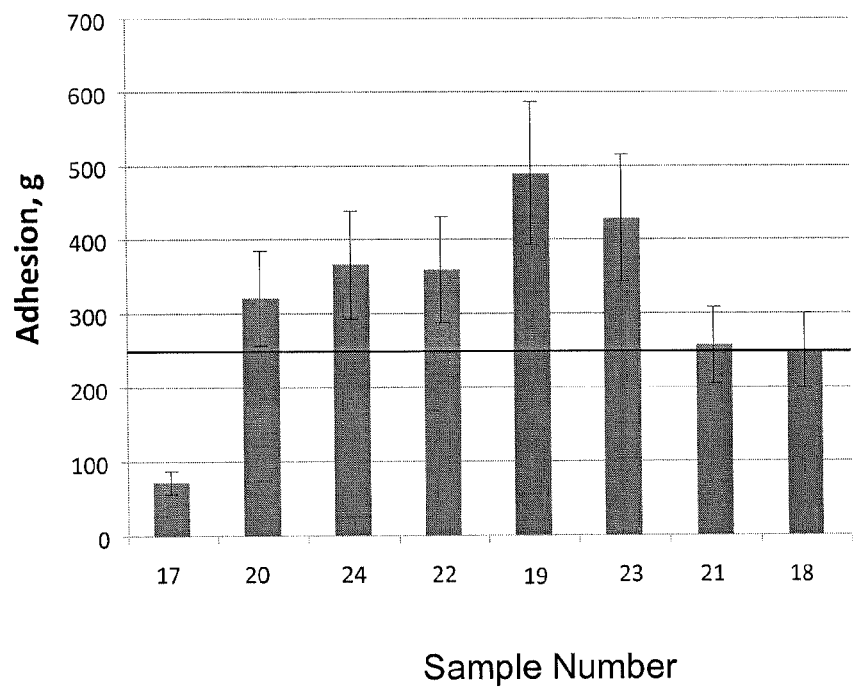
FIG. 3 presents adhesion analysis results for various samples as described in the described in the Examples below.

This synergistic effect is further illustrated in examples 17-24 where the ratio of SELVOL ULTALUX AD to SELVOL ULTALUX FA is systematically varied. Unexpectedly, it was found that intermediate ratios of SELVOL ULTALUX AD to SELVOL ULTALUX FA resulted in greatly increased adhesion compared to a film made from SELVOL ULTALUX AD or SELVOL ULTALUX FA alone. The adhesion test results for Examples 17-24 are presented graphically in FIG. 3. While each of the samples had a greater adhesion than for Sample 18 (SELVOL ULTALUX AD only), the adhesion results with the mixtures, especially for Samples 19, 22, 23, and 24 are significantly greater than would be expected by one skilled in the art based on the data for both SELVOL ULTALUX AD and SELVOL ULTALUX FA when used individually.

Table 2, above, and Table 3 illustrate adhesion as a function of PVOH copolymer content. Adhesion to glass was determined by casting a film onto a glass plate as described above, then performing a 90° peel test using a Stable Micro Systems TA.XT Plus Texture Analyzer equipped with a 90° peel rig. Skin adhesion was determined by placing a 4 inch$^2$ application of "mask" solution onto a human forearm. The solution was allowed to dry and remain in place for 2 hours. The area of film still in intimate contact with the skin after two hours was measured to determine % skin adhesion.

Tables 2 and 3 illustrate how embodiments disclosed herein may be used to 1) control adhesion as function of copolymer content, and 2) achieve adhesion that is superior to what is achieved by the most commonly used commercial grade of PVOH in face masks, SELVOL ULTALUX FA. The ability to control the adhesion properties of the mask composition may allow tailoring of the exfoliation properties of the mask, when applied, for example.

TABLE 3

| Example (above) | 1 | 4 | 8 | 10 | 11 |
|---|---|---|---|---|---|
| Adhesion to Glass, g | 32 | 250 | 57 | 75 | 490 |
| % Skin Adhesion | | | 97 | 65 | 99 |

Table 4 illustrates how embodiments disclosed herein may be used to 1) produce face masks with film attributes spanning the range of those that are commercially available simply by varying the copolymer functionality and 2) produce masks with superior characteristics to commercially available masks. The comparative samples, commercially available mask compositions, typically include 10 to 15 wt % of a polyvinyl alcohol similar to SELVOL ULTALUX FA.

Tensile Strength, Elongation at Break, and Modulus were determined for the respective films by cutting them into uniform strips of 1 inch width and measuring the tensile properties using an INSTRON Model 5542. Adhesion to glass was measured as described above. The more qualitative tactile and performance properties were determined by applying 1 ounce samples of the respective mask formulations to the face of human subjects, allowing the masks to dry over a period of 30 minutes, then peeling off. Results are illustrated in Table 4, where "+" denotes excellent performance while "−" corresponds to very poor, unacceptable, performance.

TABLE 4

| | TS, psi | EB, % | Modulus, psi | Spreading | Viscosity, cP | Peel in one Piece | Adhesion to glass, g |
|---|---|---|---|---|---|---|---|
| FREEMAN CUCUMBER* | 1086 | 198 | 1593 | + | 21,000 | + | 4 |
| EXUVIANCE REJUVENATING MASQUE | 815 | >200 | 542 | + | 4600 | + | 3 |
| QUEENE HELENE | 1671 | >200 | 2176 | −− | 250,000 | + | 20 |
| BOSCIA WHITE | 470 | 59 | 2900 | − | 40,000-80,000 | − | <10 |
| BOSCIA Black | 1000 | 181 | 3600 | − | 40,000-80,000 | − | <10 |
| MONTAGNE JEUNESSE PASSION | 2026 | 70 | >50000 | | | − | <20 |
| Example 9 | 748 | >200 | 633 | | | + | 30 |
| Example 11 | 832 | 180 | 1375 | | | + | 490 |
| Example 16 | 1581 | 200 | 2000 | | | + | 60 |
| Fully Formulated Cucumber Mellon | 1250 | >200 | 1650 | + | 6590 | + | <10 |
| Fully Formulated Fresh Flowers | 1260 | >200 | 1620 | + | 7180 | + | <10 |

Examples 9, 11, and 16 illustrate how softness and exfoliation properties of the mask compositions may be tailored. The modulus (indicative of softness) for examples 9, 11, and 16 is lower or comparable to various commercially available mask compositions, while the adhesion to glass (indicative of exfoliation properties) is greater to significantly greater than the commercially available mask compositions.

As another example of tailoring properties of the cosmetic compositions, the excellent adhesion properties of Example 19 may be used for depilatory and epilatory (hair removal) applications, where "epilatory" products and compositions as used herein are used for physical removal of the hair, whereas "depilatory" products and compositions include a chemical component to chemically break down a hair follicle during the treatment process. Current depilatory products and epilatory products require heating before use, are relatively messy, tend to have undesirable odors, and/or may be irritating to the skin. In contrast, the adhesive properties of Example 19 and similarly tailored compositions may be used more conveniently (without heating), has significantly less odor, and may remove hair as effectively, such as compared to the "best in class" commercial products "Professional Surgi Wax Brazilian Waxing Kit" or the "Sally Hansen Lavender Spa Wax Kit."

As shown by the Examples above, comonomers and amounts thereof may be selected to tailor the mechanical properties of the cosmetic compositions disclosed herein. Masks and other cosmetic compositions useful for facial care or skin care, for example, may be tailored according to embodiments herein to meet desired end product requirements, such as softness, adhesion, dissolution time, etc., by selecting the polyvinyl alcohols and polyvinyl alcohol copolymers used in the formulation. Such masks may thus provide a unique combination of adhesion (indicative of exfoliation properties) and modulus (indicative of softness), as well as peel performance, water washability, and other properties.

As an example, one of the challenges in the skin care industry is in developing a mask that provides a desired combination of tightness or softness (feel, modulus), dead skin removal (adhesion), and the ability to peel in one piece and/or be easily removed from the skin Typical compositions that are commercially available are not adherent enough to the skin to do an adequate job at exfoliation. Use of polyvinyl alcohol copolymers and tailoring of the composition as described herein may provide such a combination of properties.

A composition useful in a face or skin care mask for cleaning and exfoliating the skin while having a soft feel, according to embodiments herein, may include at least one polyvinyl alcohol copolymer and may have an adhesion to glass of at least 30 g and a modulus of less than about 1800 psi (as defined by the test methods above). Such a composition may also have one or more of a % skin adhesion of at least 95%, and a tensile strength in the range from about 190 psi to about 2000 psi. In some embodiments, the composition may have an adhesion to glass of at least 200 g. For example, the polyvinyl alcohol may include a copolymer of vinyl alcohol and vinylamine, where the composition has an adhesion to glass of at least 200 g.

Another composition useful in a face or skin care mask for treating the skin according to embodiments herein may include a mixture of a polyvinyl alcohol and a polyvinyl alcohol copolymer. The polyvinyl alcohol may have a degree of polymerization in the range from about 900 to about 1500 and a degree of hydrolysis in the range from about 87 to about 89. The polyvinyl alcohol copolymer may be a copolymer of vinyl alcohol and vinylamine and may have a degree of polymerization in the range from about 300 to about 600 and containing from about 3 mole % to about 15 mole % vinylamine. A weight ratio of the polyvinyl alcohol to the polyvinyl alcohol copolymer may be in the range from about 15:85 to about 65:35, such as in the range from about 20:80 to 60:40 or from about 25:75 to about 55:45. The composition may also have at least one of an adhesion to glass of at least 300 g and a modulus of less than 1500 psi.

As another example, one of the challenges in the skin care industry is to provide an epilatory composition that is easy to apply, easy to remove, and has little or no odor. Typical compositions that are commercially available are not adherent enough to the skin to do an adequate job at hair removal. Use of polyvinyl alcohol copolymers and tailoring of the composition as described herein may provide such a combination of properties.

A composition useful in a drip-free face or skin care mask according to embodiments herein may include a polyvinyl alcohol and various additives. A composition useful in a face or skin care mask for removing hair, such as an epilatory according to embodiments herein, may include a polyvinyl alcohol copolymer comprising a copolymer of vinyl alcohol and vinylamine. To provide effective hair removal, the composition may have an adhesion to glass value of at least 400 g; at least 500 g in other embodiments; and at least 600 g in yet other embodiments. A composition useful in a pore strip or keratonic plug remover according to embodiments herein may include a polyvinyl alcohol copolymer comprising a copolymer of vinyl alcohol and vinylamine. To provide effective treatment, the pore strip or depilatory composition may have an adhesion to glass value in the range from about 150 to about 350 g. There exists a need for epilatory, pore strips and other cosmetic compositions to be essentially "drip-free," resulting in easy application and less mess than traditional products. There also exists a need for pore strips and epilatories that conform to the body such as the contours around the nose and mouth without being hindered by a backing strip. Tables 5-7 below illustrate exemplary drip-free compositions that may be used in cosmetic compositions such as pore strips and epilatories, as well as measured properties of the composition and films resulting from such compositions.

In Table 5, four exemplary drip-fee face mask examples are shown. A variety of common thickening agents can be used to achieve drip-free facial masks. By comparing the compositions of Table 5 to the commercially available face masks in Table 5A, it is noted that examples 28-31 all peel in essentially one piece, dry quickly are drip free and easy to spread and cause no pain upon removal while none of the commercially available products meet all of these requirements. The compositions in Table 6 have the precise adhesion necessary to remove keratonic plugs (compare to the commercial products in Table 6A), while minimizing undue pain to the user. The adhesion of the comparative sample Example in Table 6 is not great enough to effectively remove keratonic plugs. Composition 33 is superior to the commercially available pore strips in Table 6A because it tears in one piece and does not require a backing strip (can effectively shape to the contours of the face). In Tables 7 and 7A, it is demonstrated that Compositions 34-36 achieve adhesion on par with commercial products, while having the advantage of not requiring a backing strip. In the tables below, ●=Best, O=Good, Δ=acceptable, and X=not acceptable.

TABLE 5

Face Mask Examples

| | FACE MASKS Example | | | |
|---|---|---|---|---|
| | 28 | 29 | 30 | 31 |
| Fast Drying Time (≤20 min) | O | O | O | O |
| Peels in essentially One Piece | O | Δ | O | O |
| Tensile Strength | 1070 | 1291 | 1230 | 2590 |
| Modulus | 1900 | 2428 | 2018 | 2300 |
| TS/Modulus | 0.56 | 0.53 | 0.61 | 1.13 |
| Elongation at Break | 166 | 175 | 172 | >200 |
| Drip Free | ● | ● | ● | ● |
| Easy to Spread | O | O | O | O |
| Viscosity | >100,000 | >40,000 | >20,000 | >80,000 |
| Brookfield Yield Value | 120 | 23 | 5 | 99 |
| No Pain On Removal | O | O | O | O |
| Adhesion to Glass | 2 | 3 | 2 | 32 |
| Composition: Polymer | | | | |
| Ultalux FF | 13 | 13 | 13 | |
| Ultalux FA | | | | 12 |
| Ultalux AD | | | | |
| Solvent | | | | |
| Water | 68.6 | 69.5 | 69 | 69.4 |
| Ethanol | 12 | 12 | 12 | 12 |
| Plasticizer | | | | |
| Propylene Glycol | | | | |
| Glycerin | 5 | 5 | 5 | 5 |
| PEG 400 | | | | |
| MPEG 350 | | | | |
| Thickener | | | | |
| HEC (Natrosol) | | 0.5 | | |
| Carbopol 980/TEA | | | | 0.6 |
| Laponite XLG | | | 1 | |

TABLE 5-continued

Face Mask Examples

| FACE MASKS Example | 28 | 29 | 30 | 31 |
|---|---|---|---|---|
| Xanthan Gum | 0.4 | | | |
| Fragrance | 0.5 | | | 0.5 |
| Preservative | 0.5 | | | 0.5 |

TABLE 5A

Comparative (Commercially available) Face Mask Examples

| FACE MASKS | Freeman Cucumber | Exuviance | Merlot Grapeseed | Boscia Black | Boscia White | Queene Helene | Montagne Jeunesse |
|---|---|---|---|---|---|---|---|
| Fast Drying Time (<20 min) | ○ | ○ | ○ | Δ | ● | Δ | Δ |
| Peels in essentially One Piece | ○ | ○ | ○ | Δ | Δ | Δ | Δ |
| Tensile Strength | 1086 | 815 | 1066 | 1000 | 470 | 1671 | 2026 |
| Modulus | 1593 | 542 | 6170 | 3600 | 2900 | 2176 | 50000 |
| TS/Modulus | 0.68 | 1.50 | 0.17 | 0.28 | 0.16 | 0.77 | 0.04 |
| Elongation at Break | 198 | >200 | 123 | 181 | 59 | >200 | 70 |
| Drip Free | ○ | Δ | Δ | ● | ● | ● | X |
| Easy to Spread | ○ | ○ | ○ | ○ | ○ | Δ | ○ |
| Viscosity | 21000 | 4600 | ~5000 | >150,000 | >150,000 | >250,000 | ~4000 |
| Brookfield Yield Value | ○ | ○ | ○ | >500 | >500 | n/a | ○ |
| No Pain On Removal | ○ | ○ | ○ | ○ | ○ | ○ | ○ |
| Adhesion to Glass | 4 | 3 | <10 | <10 | <10 | 20 | <20 |

TABLE 6

Pore Strip Examples and Comparative Example

| | PORE STRIP Example Number | | Comparative Example from U.S. Pat. No. 6,159,493 |
|---|---|---|---|
| | 32 | 33 | |
| Fast Drying Time (<15 min) | Δ | ○ | ● |
| Peels in essentially One Piece | ○ | ○ | ○ |
| Tensile Strength | 1537 | 2026 | 8200 |
| Modulus | 2046 | 3301 | 592437 |
| Elongation at Break | 183 | 173 | 20 |
| Drip Free | X | ○ | Δ |
| Easy to Spread | ○ | ○ | ○ |
| Viscosity | 3300 | >40,000 | >25,000 |
| Brookfield Yield Value | 0 | 50 | 4 |
| Adequate Adhesion to Remove Keratonic Plugs | ○ | ○ | X |
| Adhesion to Glass | 312 | 311 | 60 |
| Composition: | | | |
| Polymer | | | |
| Ultalux FF | | 6 | 5 |
| Ultalux FP | | | 10 |
| Ultalux FA | 6 | | |
| Ultalux AD | 6 | 6 | |
| PVP K90 | | | 10 |
| Solvent | | | |
| Water | 72.5 | 72.5 | 75 |
| Ethanol | 10 | 10 | |
| Plasticizer | | | |
| Glycerin | 2 | 2 | |
| Thickener | | | |
| Laponite XLG | 0.5 | 0.5 | |
| Surfactant | | | |
| Polysorbate-20 | 1 | 1 | |
| Emollient | | | |
| Emu Oil | 2 | 2 | |

TABLE 6A

Comparative (Commercially available) Pore Strip Examples

| | PORE STRIP Comparative Pore Strip Examples | |
|---|---|---|
| | Japanese Pore Clear Pack | Boscia Pore Purifying Black Strips |
| Fast Drying Time (<15 min) | ● | n/a |
| Peels in essentially One Piece | Δ | n/a |
| Tensile Strength | 3780 | n/a |
| Modulus | 164022 | n/a |
| Elongation at Break | 93 | n/a |
| Drip Free | ○ | n/a |
| Easy to Spread | Δ | n/a |
| Viscosity | >40,000 | n/a |
| Brookfield Yield Value | >40 | |
| Adequate Adhesion to Remove Keratonic Plugs | ○ | ○ |

TABLE 6A-continued

Comparative(Commercially available) Pore Strip Examples

| | PORE STRIP Comparative Pore Strip Examples | |
| --- | --- | --- |
| | Japanese Pore Clear Pack | Boscia Pore Purifying Black Strips |
| Adhesion to Glass | 313 | 230 |

Values designated n/a above were not measured due to a heavy backing strip. The other products in this category can be spread on skin, and do not require a backing strip.

TABLE 7

Epilatory Examples

| | EPILATORY Example Number | | |
| --- | --- | --- | --- |
| | 34 | 35 | 36 |
| Fast Drying Time(<15 min) | ○ | ○ | ○ |
| Peels in essentially One Piece | ○ | ○ | ○ |
| Tensile Strength | 1800 | 2000 | 3100 |
| Modulus | 3492 | 2710 | 8693 |
| Elongation at Break | 106 | 100 | 100 |
| Drip Free | ○ | ○ | ○ |
| Easy to Spread | ○ | ○ | ○ |
| Viscosity | >25000 | >25000 | >25000 |
| Adequate Adhesion to Remove Hair | ● | ● | ● |
| Adhesion to Glass | 860 | 960 | 545 |
| Composition: Polymer | | | |
| Ultalux FF | 8 | 8 | 8 |
| Ultalux AD | 7 | 7 | 7 |
| Solvent | | | |
| Water | 67 | 67 | 72 |
| Ethanol | 12 | 12 | 12 |
| Plasticizer | | | |
| PEG 400 | | | 5 |
| MPEG 350 | 5 | | |
| Thickener | | | |
| HEC (Natrosol) | 1 | 1 | 1 |

TABLE 7A

Comparative (Commercially available) Epilatory Examples

| | EPILATORY Comparative Epilatory Examples | |
| --- | --- | --- |
| | Nads Body Wax Strips | Completely Bare Wax Strips |
| Adequate Adhesion to Remove Hair | ● | ● |
| Adhesion to Glass | 621 | 845 |

As another example of the utility of the unexpected synergistic adhesion effect meeting a challenge of the cosmetic industry, a blend of SELVOL ULTALUX AD and SELVOL ULTALUX FA with a polyvinylpyrrolidone can be used to make a longer lasting, smudge resistant eye liner. An eyeliner formulation was prepared according to the formulation provided in Table 8 and compared to two additional formulations. Comparative Sample 26 is similar to the formulation described in US5013543. Comparative Sample 27 is formulation using PVP and PVOH. The results of the comparison are shown in Table 9.

TABLE 8

| Ingredient (wt %) | Sample 25 | Comp. Sample 26 | Comp. Sample 27 |
| --- | --- | --- | --- |
| Water | 40 | 40 | 40 |
| Iron Oxide | 25 | 25 | 25 |
| PVP | 18 | 23 | 18 |
| Selvol ™ Ultalux ™ FA | 2.5 | — | 5 |
| Selvol ™ Ultalux ™ AD | 2.5 | — | — |
| Ethanol | 5 | 5 | 5 |
| Propylene Glycol | 5 | 5 | 5 |
| Polysorbate-20 | 1.5 | 1.5 | 1.5 |
| Germaben | 0.5 | 0.5 | |

TABLE 9

| Formulation | Sample 25 | Comp. Sample 26 | Comp. Sample 27 |
| --- | --- | --- | --- |
| Skin Adhesion | ● | ○ | Δ |
| Smudge/Smear Resistance | ○ | ○ | Δ |

Skin adhesion tests were performed as described above. The smudge/smear resistance test was performed similar to that as described in U.S. Pat. No. 4,423,031 by Murui and Saitoh. As shown by the results in Table 8, the use of a mixture of PVOH copolymers may provide for superior adhesion and a longer lasting eyeliner composition.

The ability to tailor properties of cosmetic compositions according to embodiments herein is further illustrated in FIGS. 4-17, discussed below.

Figure 4:
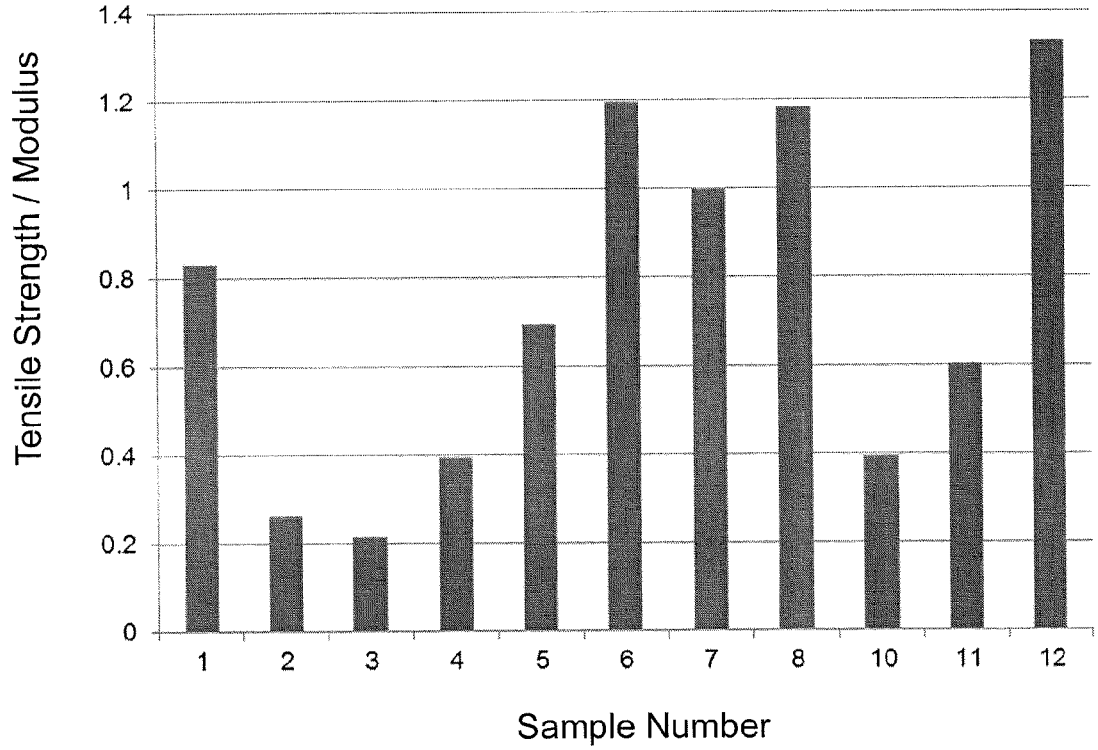
FIGS. 4-18 present analyses results for various samples as described in the Examples below.
Figure 5:
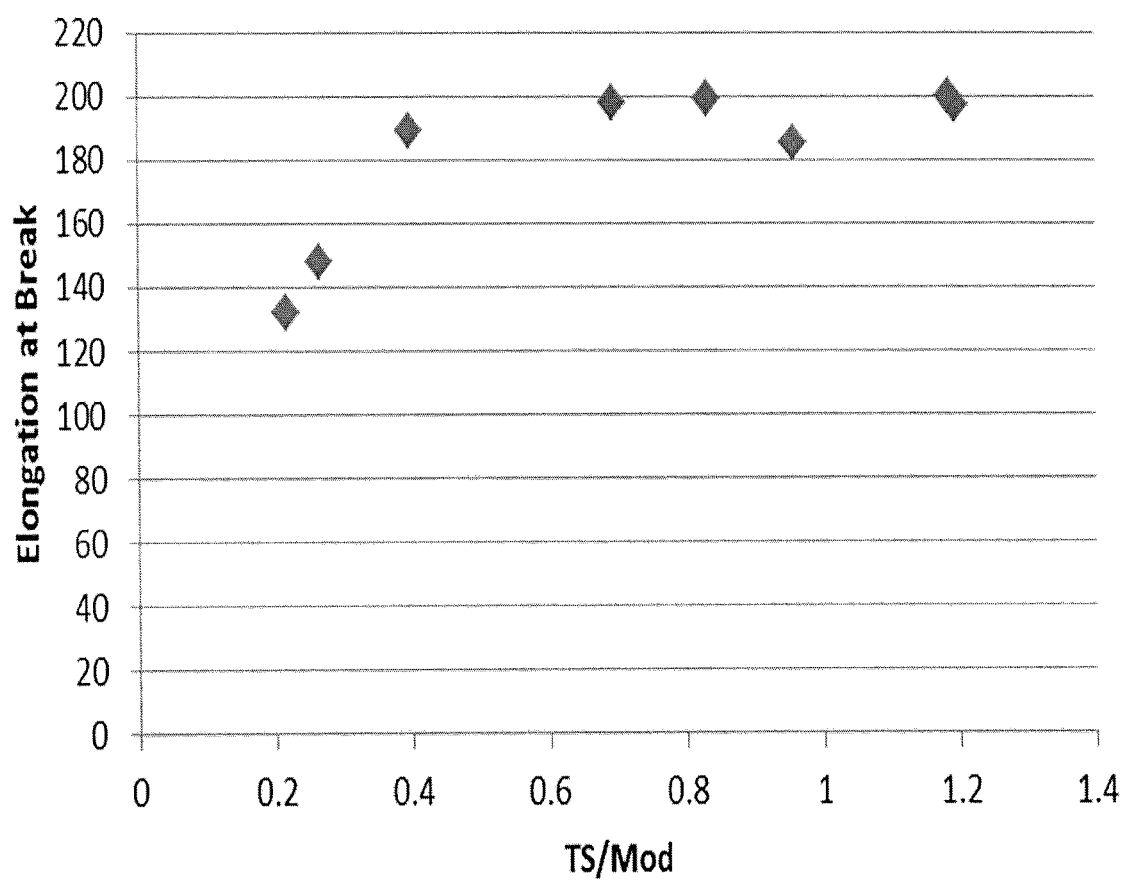

Referring now to FIG. 4, the ratio of tensile strength to modulus for several of the above samples is graphically illustrated. Tensile strength for the various samples ranged from a low of less than 200 psi to a high of about 1200 psi; modulus ranged from 160 psi up to 3150 psi. The type of polyvinyl alcohol polymer, polyvinyl alcohol copolymer, or mixture thereof used in the composition may thus result in a wide range of tensile strength and modulus. The ratio of tensile strength to modulus (TS/M) may be indicative of the cohesiveness of the film resulting from the cosmetic composition. It is hypothesized that films having a low TS/M ratio may tend to flake or tear easily, while those with a high TS/M ratio may peel from the skin in essentially one piece. Trends may also be shown relating TS/M ratio to elongation at break, where a TS/M ratio of at least 0.6 or at least 0.7 may be associated with an elongation at break of at least 180%, which may also be indicative of the film being able to peel from the skin in essentially one piece when the product is allowed to dry for only 10 to 15 minutes, as is commonly instructed on packaging for commercial products. This is illustrated in FIG. 5, a plot of Elongation at Break vs. TS/Mod for examples 1-8 from Table 2 (note: the Elongation at Break values are capped at 204 by the analytical instrument used, and the >200 values in Table 2 are shown in FIG. 5 as "200"). The ability to properly select polymers, copolymers, or mixtures thereof to result in desired TS/M ratios and Elongation values may be useful in designing cosmetic compositions that may peel in essentially one piece.

Properties of the cosmetic compositions may also be tuned by appropriate selection of the additives, such as the plasticizer. Numerous samples were made using SELVOL ULTALUX FA and various plasticizers of varying compositional ranges according to the following table.

TABLE 10

| INGREDIENT | Weight % |
|---|---|
| SELVOL ™ ULTALUX FA | 14 |
| Ethanol | 12 |
| Plasticizer | 1 to 10 |
| Water | Balance |

The plasticizers used are illustrated in the following table.

TABLE 11

| Name | Structure | Weight % OH |
|---|---|---|
| PEG 300 | HO(CH₂CH₂O)$_n$H | 11.3 |
| PEG 400 | HO(CH₂CH₂O)$_{n+2}$H | 8.7 |
| PEG 600 | HO(CH₂CH₂O)$_{n+6}$H | 5.7 |
| PEG 1000 | HO(CH₂CH₂O)$_{n+15}$H | 3.4 |
| MPEG 350 | H₃CO(CH₂CH₂O)$_{n+1}$H | 4.9 |
| Glycerin | HOCH₂CH(OH)CH₂OH | 55.4 |
| Propylene Glycol | HOCH₂CH(OH)CH₃ | 44.7 |
| Butylene Glycol | HOCH₂CH₂CH(OH)CH₃ | 37.8 |
| Dextrose | (glucose structure) | 37.8 |

Figure 7:
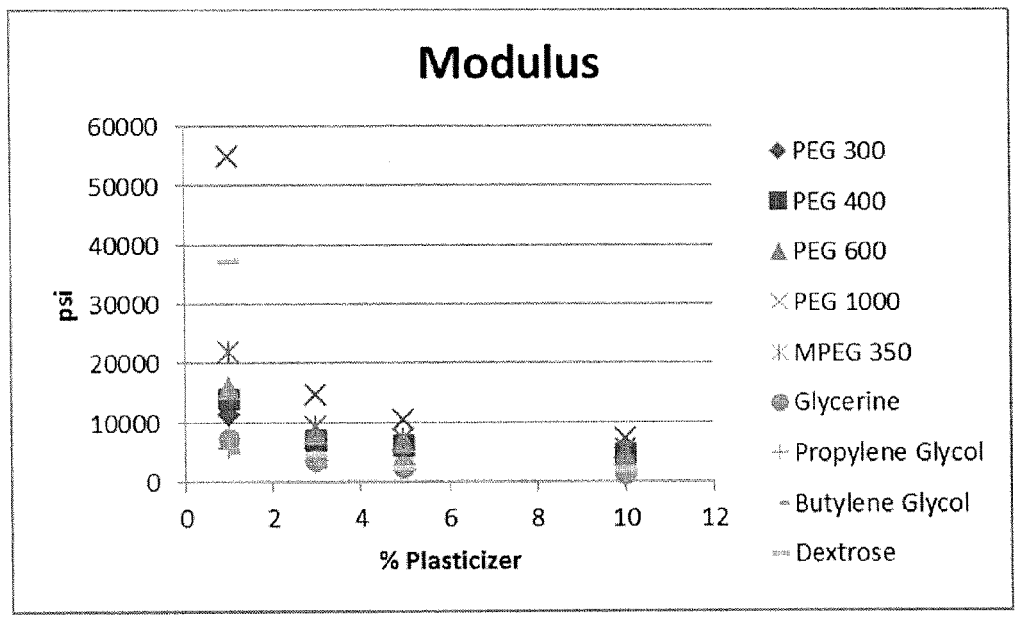
Figure 8:
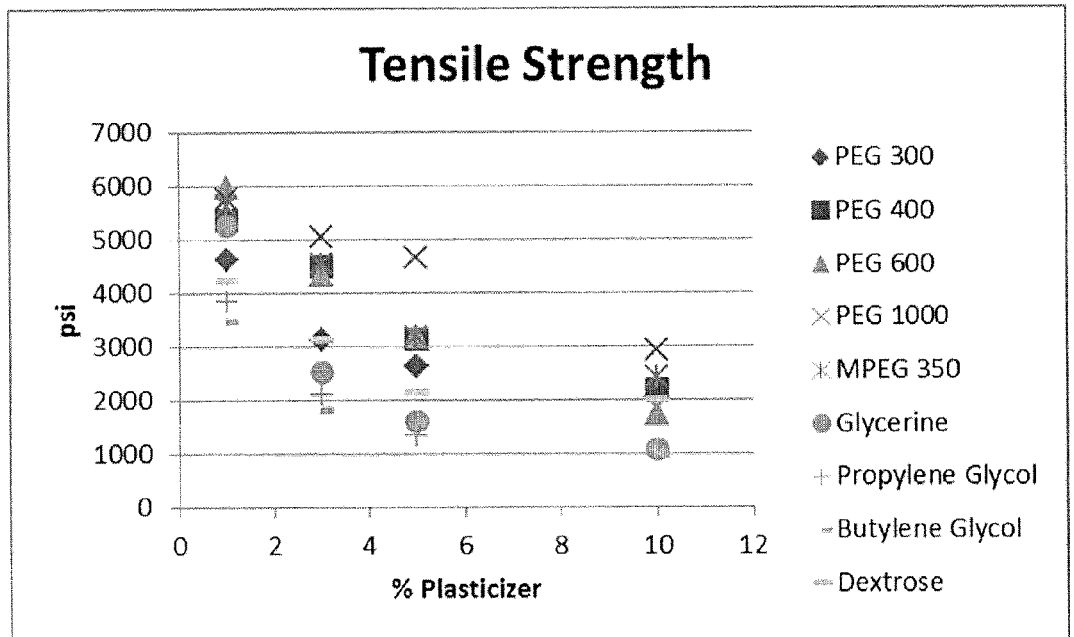
Figure 9:
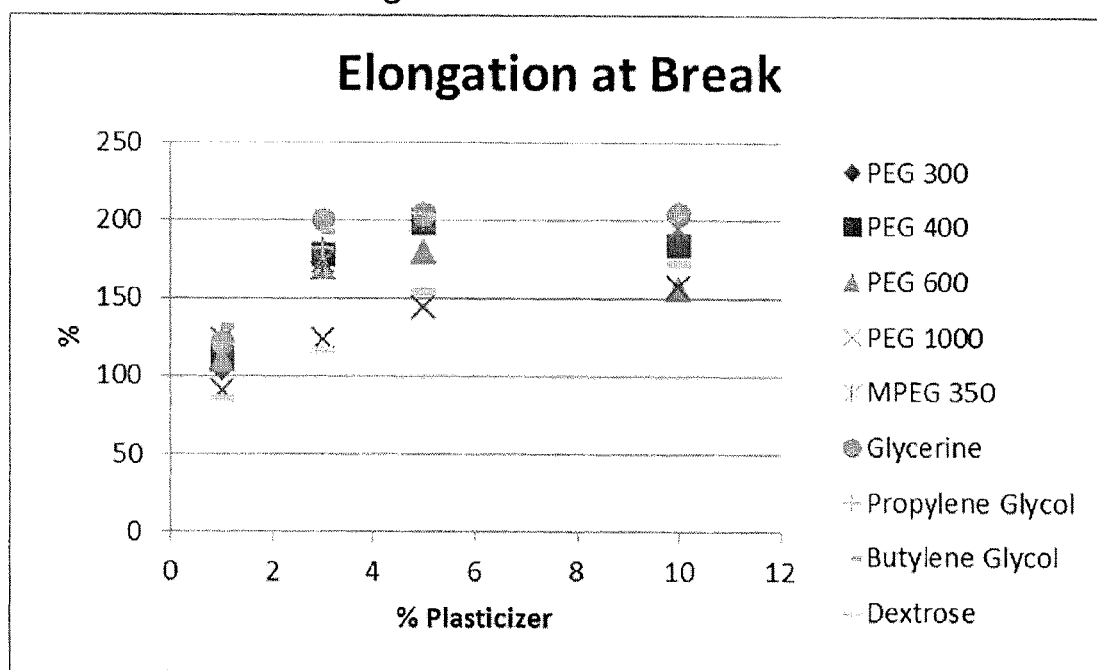

Films of the samples were then produced and analyzed as described above. The properties of the resulting films as a function of plasticizer and plasticizer content are illustrated in FIGS. 7-9. In general it is observed that tensile strength and modulus decrease with increasing plasticizer content, and elongation at break increases with increasing plasticizer content. The overall impact of a particular plasticizer and content may vary greatly, however, as illustrated in FIG. 7 with respect to modulus. Use of 1% plasticizer in an otherwise constant composition, for example, may result in modulus values ranging from less than 5000 psi to greater than 50000 psi. Proper selection and tailoring of a composition according to embodiments herein may thus minimize the amount of trial and error associated otherwise associated with randomly formulating and testing to arrive at a useful cosmetic composition.

The effect of other plasticizers may also be anticipated based on an analysis of the data illustrated in FIGS. 7-9. The size, hydroxyl group content, geometry, and hydrodynamic volume of the plasticizer, as well as how the plasticizer coils and behaves in solution may impact the properties of cosmetic compositions. Knowledge of such relationships may be advantageously used according to embodiments herein to tailor properties of a cosmetic composition.

Figure 10:
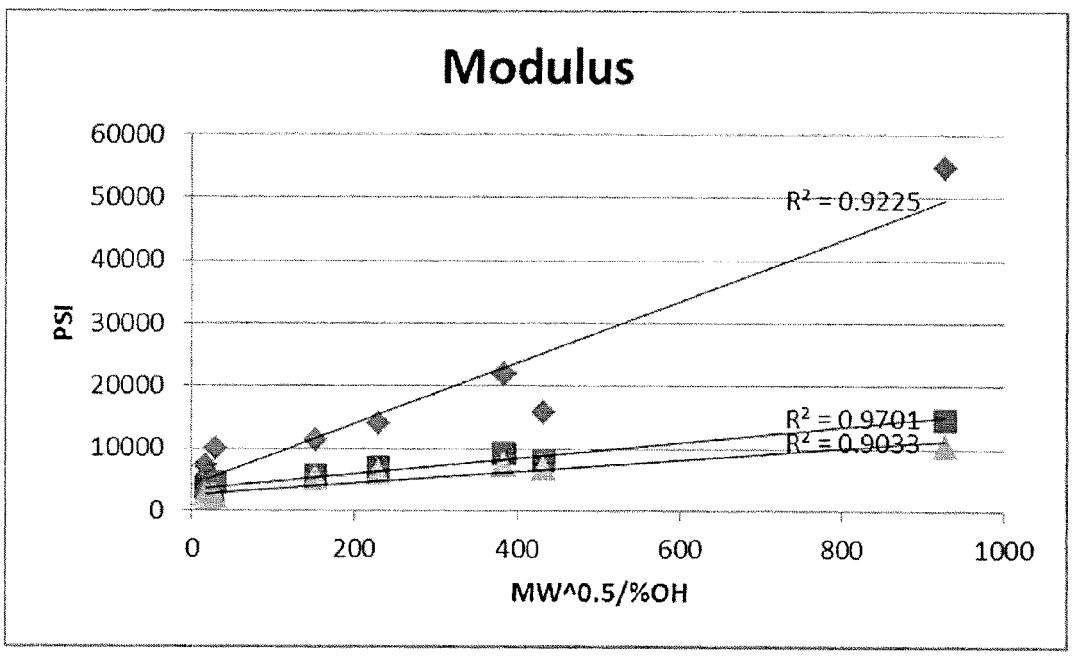

For example, modulus and tensile strength may have an inverse relationship with respect to the weight % terminal OH groups in the plasticizer, modulus and tensile strength may have a proportional relationship with respect to plasticizer size (molecular weight), and elongation at break may be proportional with respect to % terminal OH groups in the plasticizer. As illustrated in FIG. 10, plotting modulus (in psi) versus the ratio of the square root of the molecular weight of the plasticizer to the weight percent OH results in a linear fit having an $R^2$ value of greater than 0.9 (indicative of a good fit). Thus, for a given polyvinyl alcohol or polyvinyl alcohol copolymer, the plasticizer and amount thereof may be selected to result in a desired modulus. Similar correlative relationships may also exist for tensile strength, TS/M ratio, and elongation, may be stored in the data store, as well as between various properties, and these relationships may be used effectively to select components and tailor the compositions to meet desired results.

Table 4 above also includes two fully formulated face mask formulations that illustrate the utility of understanding the relationship between additive content (e.g., plasticizer, fragrance, preservatives, etc.) and resulting mask properties. The Cucumber Mellon and the Fresh Flowers fully formulated products have the following composition:

TABLE 4A

| INGREDIENT | WEIGHT % |
|---|---|
| Water | 66.5 |
| Selvol ™ Ultalux FA | 13 |
| Ethanol | 12 |
| Glycerin | 3 |
| Propylene Glycol | 3 |
| Fragrance | 1 |
| Polysorbate-20 (surfactant) | 1 |
| Preservative | 0.5 |

Figure 6:
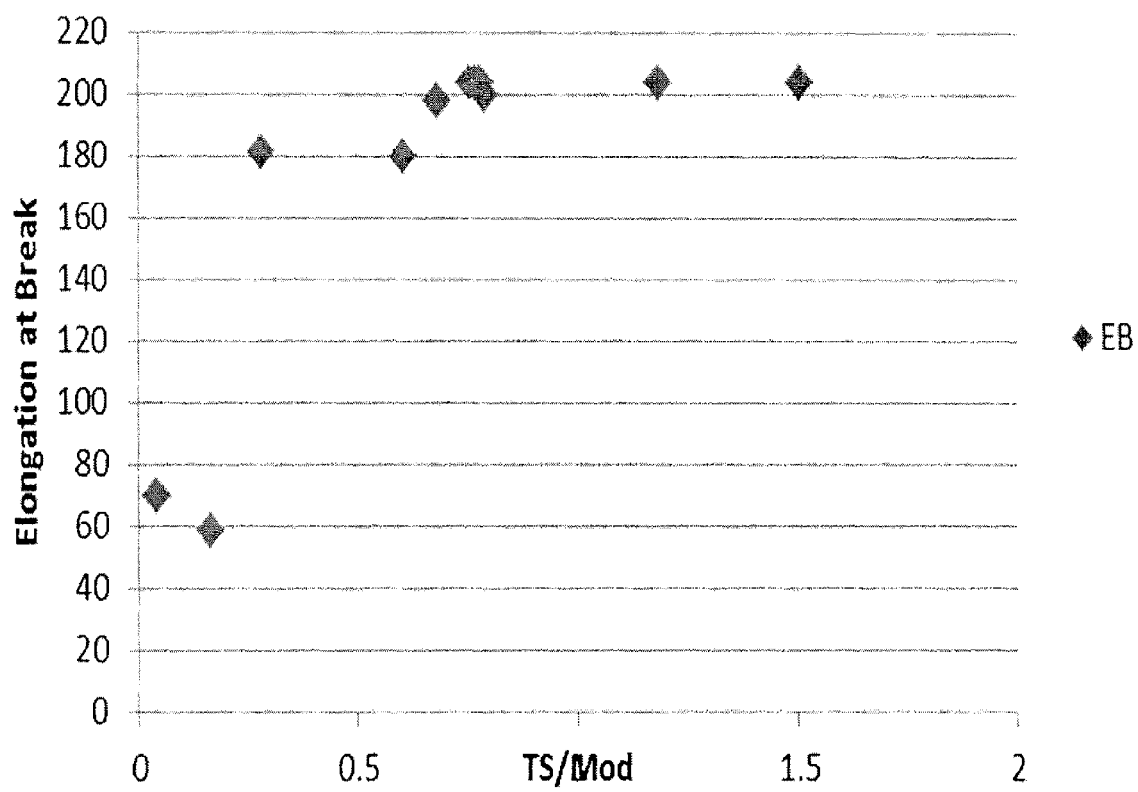

These fully formulated samples buttress the simulated face mask results and further illustrate that working face mask products may be designed or tailored according to embodiments herein to have a desired set of properties, as illustrated by TS/MOD, Elongation at break, ability to peel in one piece, feel, etc. FIG. 6 is a plot of Elongation at Break vs. TS/Mod for the examples from Table 4, including the fully formulated samples.

The effect of plasticizer on adhesion was also studied. Several samples were formulated using one of SELVOL ULTALUX FA, SELVOL ULTALUX AD, or SELVOL ULTALUX SC according to the formulations shown in Table 12.

TABLE 12

| INGREDIENT | Weight % |
|---|---|
| Polymer | 12 |
| Ethanol | 12 |
| Plasticizer (propylene glycol) | 1 to 10 |
| Water | Balance |

Figure 11:
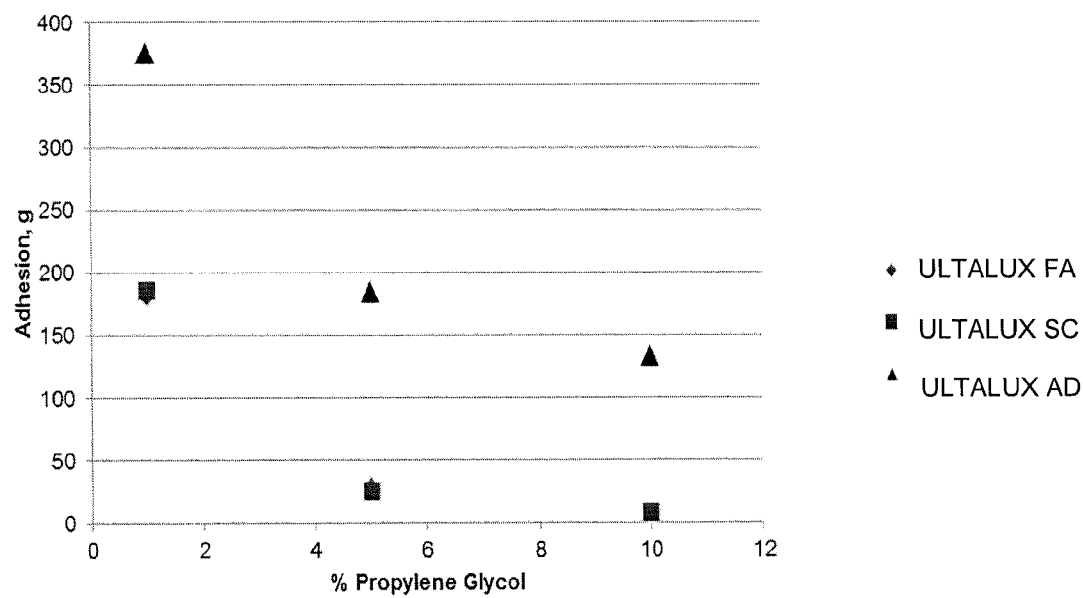

Films of the samples were then produced and analyzed as described above. The adhesive properties of the films are illustrated in FIG. 11. Adhesion decreases with increasing propylene glycol content, however the adhesion of the film may vary greatly.

Figure 12:
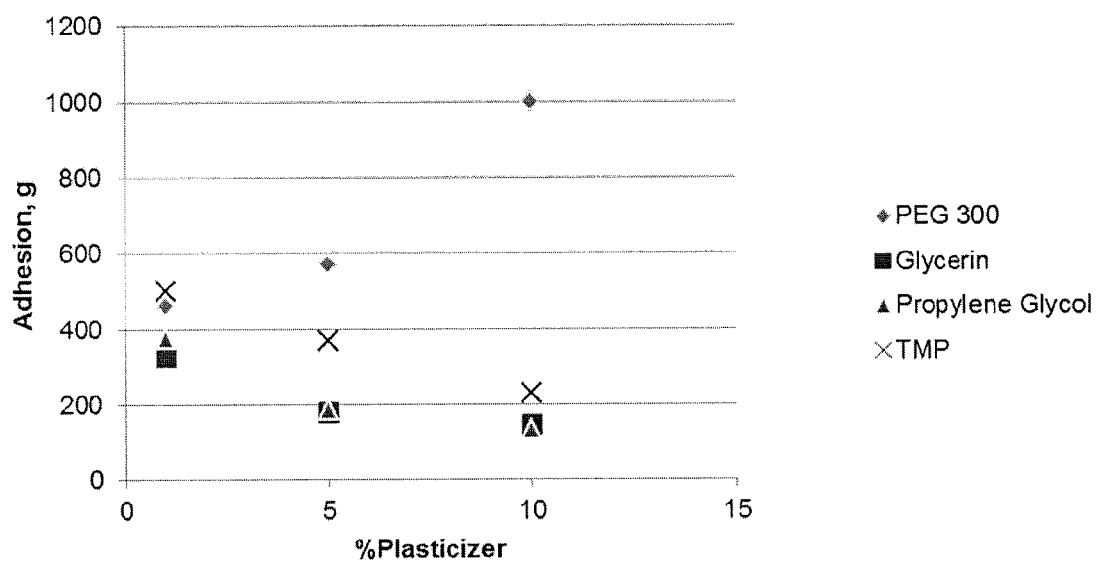
Figure 13:
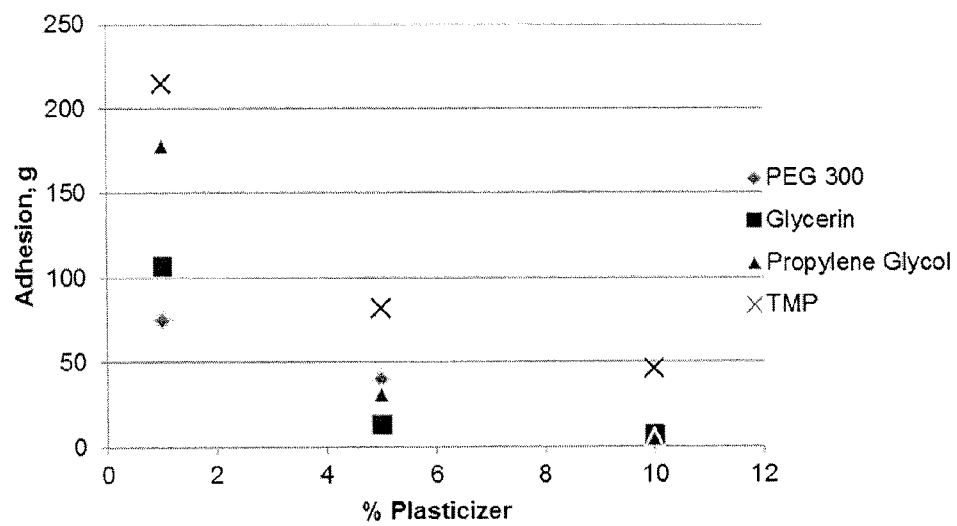

The adhesion properties may also vary in unexpected ways, depending upon the comonomer used. The effect of plasticizer on formulations using SELVOL ULTALUX AD was studied, the compositions formulated similar to that shown in Table 11 above. Films of the samples were then produced and analyzed as described above. The adhesive properties of the films are illustrated in FIG. 12. Adhesion values for glycerin, propylene glycol, and TMP (trimethylolpropane) decreased with increasing plasticizer content. However, for PEG 300, the adhesion values for the amine copolymer increased with increasing plasticizer content. This may be a result of the manner in which the plasticizer orients itself within the composition or other chemical interactions with the amine groups of the copolymer. Comparatively, FIG. 13 illustrates adhesion results for similar formulations using SELVOL ULTALUX FA, in which the PEG 300 plasticizer did not show an increasing adhesion value with increasing plasticizer content.

Figure 14:
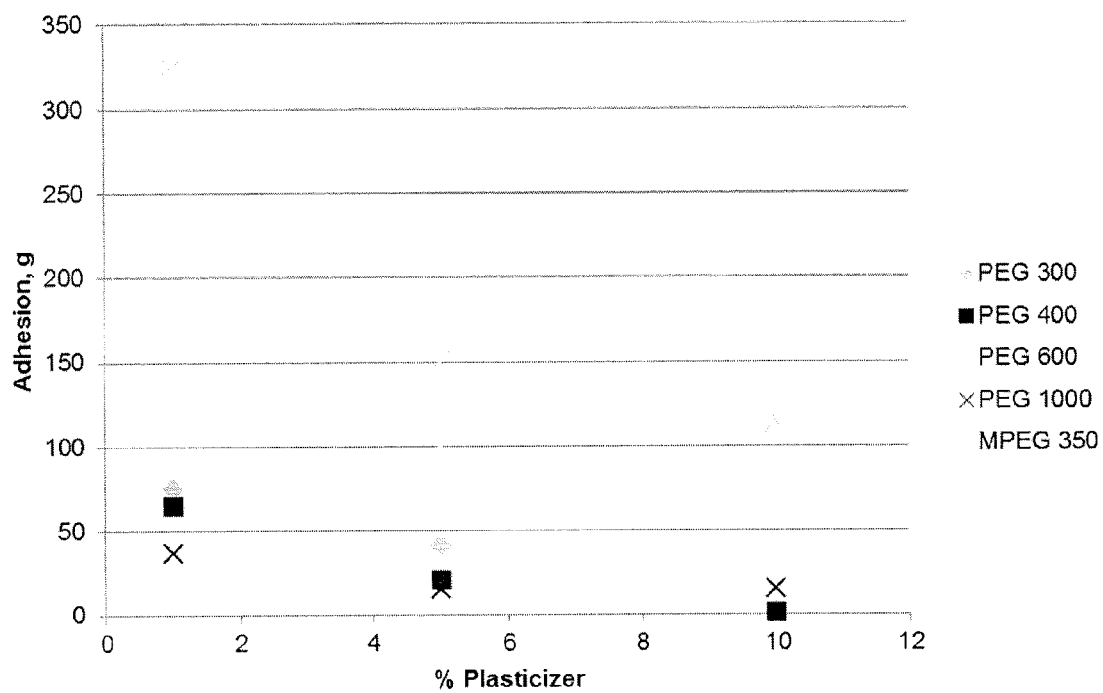
Figure 15:
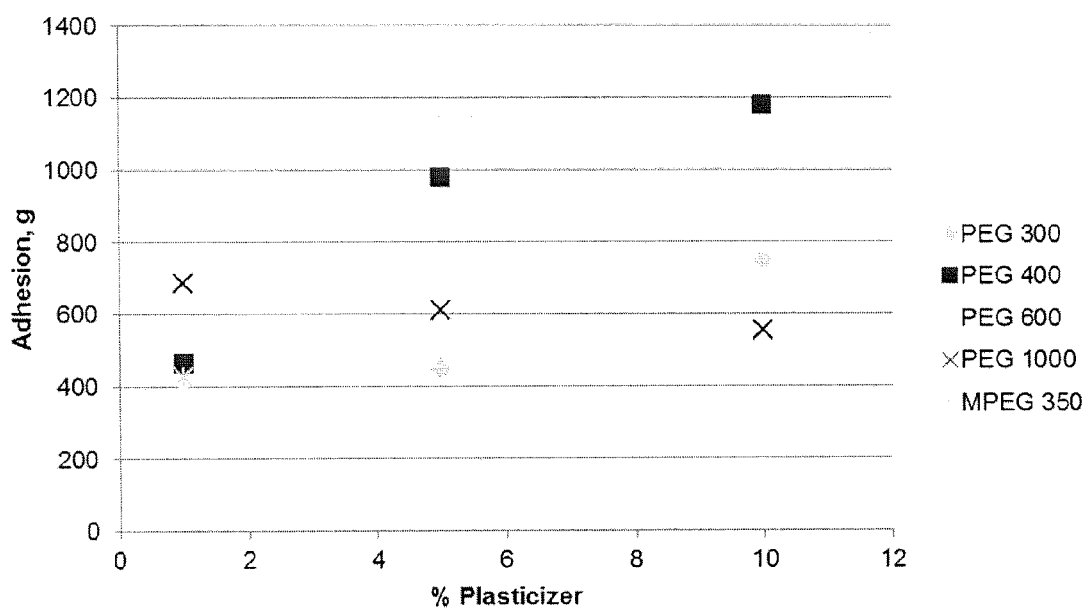
Figure 16:
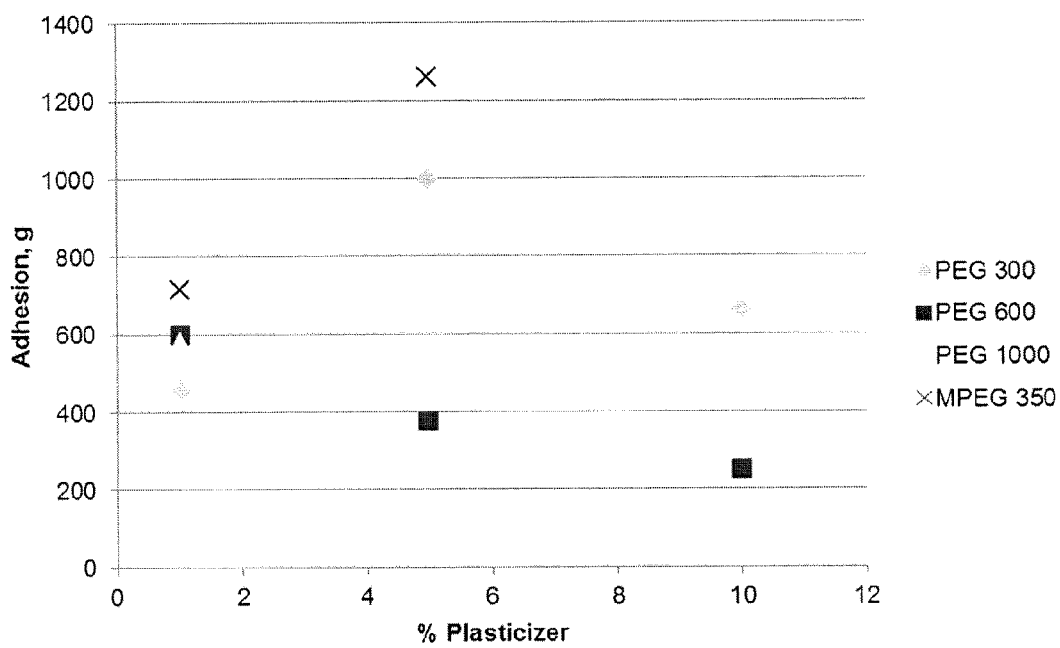

As described above with respect to FIG. 3, mixtures of SELVOL ULTALUX FA and SELVOL ULTALUX AD showed synergistic results with respect to adhesion, the mixtures having adhesion values greater than expected based on the results for the individual polymers. FIGS. 14-16 show additional results for SELVOL ULTALUX FA (FIG. 14), SELVOL ULTALUX AD (FIG. 15) and a 50:50 mixture of the two (FIG. 16) with various plasticizers formulated similar to Table 11 and analyzed as described above. The effect of the plasticizer on adhesion is clearly dependent upon the interaction between the polymer, copolymer, and plasticizer. This is further exemplified in Examples 34-36 above, where removal of the plasticizer in Example 36 results in a marked decrease in adhesion to glass, and adding a plasticizer having a high OH content results in a decrease in adhesion from greater than 500 g to less than 350 g, although it is noted that the thickening agent and polymer ratios vary slightly within these samples.

Figure 18:
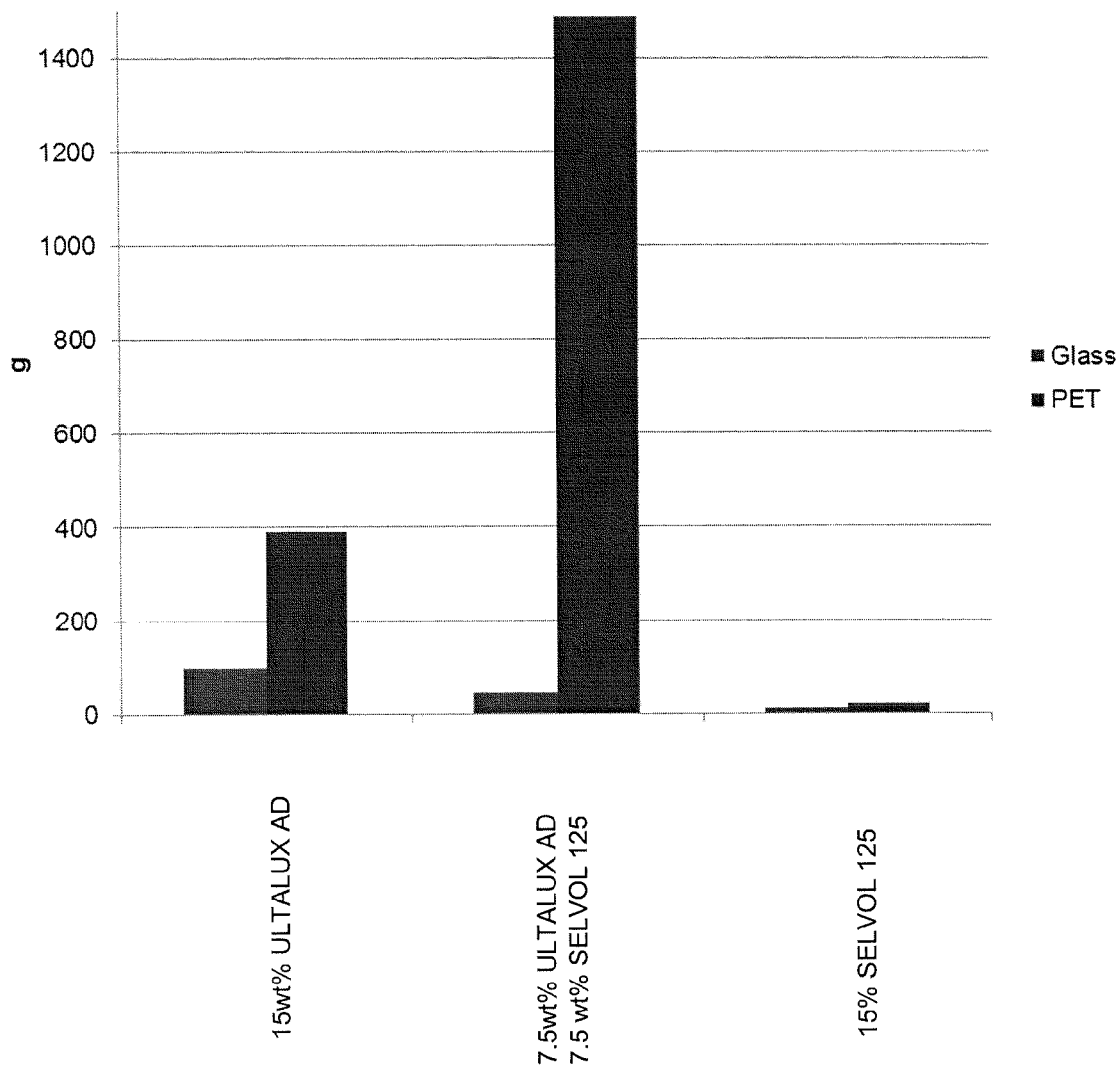

The synergistic effect of adhesion is also illustrated in FIG. 18. Three compositions were made including 82 wt % water, 15 wt % polymer, and 3 wt % Polysorbate 20. The polymers investigated included ULTALUX AD, Selvol™ 125, a high molecular weight grade of polyvinyl alcohol with over 99% hydrolysis and a 4% solution viscosity at room temperature of 28-32 cPs and an equal mixture of ULTALUX AD and Selvol™ 125. The compositions were applied to two substrates, glass and PET, and the adhesive properties were measured as described above. As illustrated in FIG. 18, the adhesion on PET of Selvol™ 125 is less than that for ULTALUX AD, and the adhesion of the mixture is intermediate that of both the individual compositions. In contrast, the adhesion on glass for Selvol™ 125 is less than that for ULTALUX AD, but the adhesion of the mixture is significantly greater than that of both the individual compositions. FIG. 18 illustrates how the mixtures used may be tailored to achieved desired properties for varying substrates.

Figure 17:
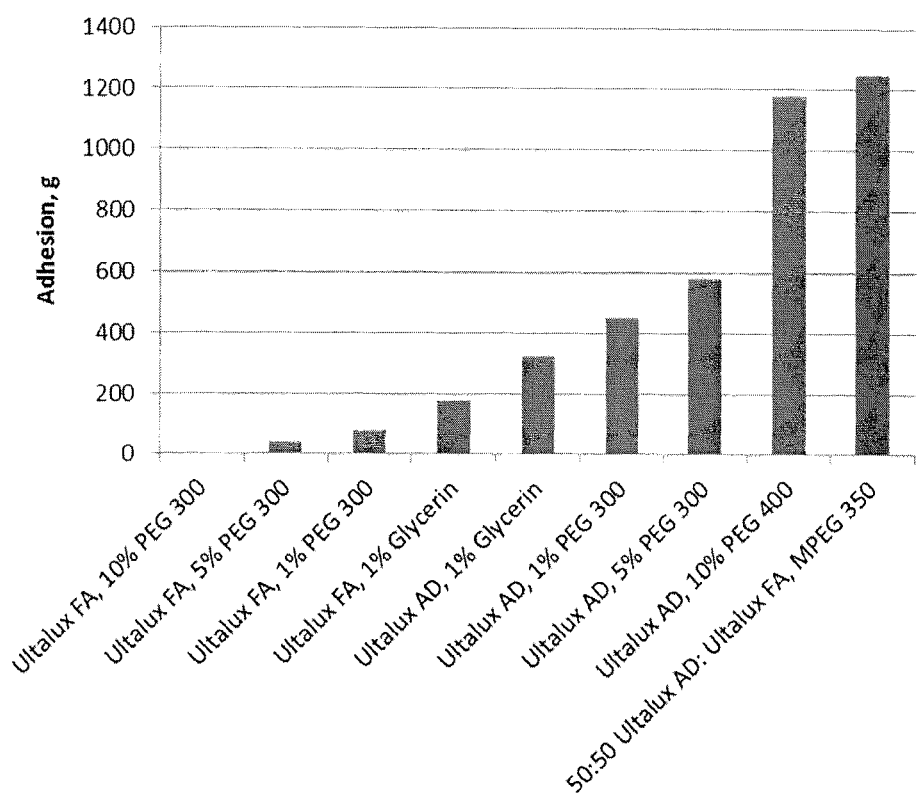

The relative effect of the plasticizer and polymer(s) may thus be dependent upon the plasticizer size, OH content, intended substrate properties, and other properties discussed above, as well as the nature of the polyvinyl alcohol polymers or copolymers being used. These effects may be advantageously used to tailor adhesion properties over 3 orders of magnitude, as shown in FIG. 17, and may be used to tailor properties of cosmetic compositions according to embodiments herein, including the exfoliating properties of face masks, improving epilatories, providing longer lasting color cosmetics, and optimizing keratonic plugs. The tailoring of such compositions may be further illustrated in Table 13, below.

TABLE 13

| | | | | |
|---|---|---|---|---|
| Water | 78 | 78 | 79.6 | 79 |
| ULTALUX AD | 6 | 6 | 0 | 6 |
| ULTALUX FA | 6 | 6 | 12 | |
| SELVOL 540 | | | | 6 |
| Ethanol | 8 | 8 | 8 | 8 |
| Xanthan Gum | 2 | | | |
| HEC | | 2 | | |
| LAPONITE XLG | | | | 1 |
| Carbopol | | | 0.2 | |
| TEA (triethanolamine) | | | 0.2 | |
| Viscosity (cP) | 10,000 | 13,000 | 40,000 | 40,000 |
| Brookfield Yield Value (cP) | ~50-70 | ~60 | ~120 | ~100 |
| Adhesion (g) | 330 | 135 | 30 | 310 |

Table 13 illustrates how a minor variation in thickener and polymer type may result in a large swing in adhesive properties, viscosity, and yield values. Formula C is akin to a drip-free face mask (exfoliating face masks, for example), having a sufficient viscosity and yield value, and a relatively low adhesion to glass. Formula B has an adhesion near the lower limit desired for use in pore strips and keratonic plugs, and Formulas A and D having an adhesion near the upper limit desired for use in pore strips and keratonic plugs.

As described above, polyvinyl alcohols and polyvinyl alcohol copolymers, such as those including amide comonomers, pyrrolidone comonomers, and sulfonic acid copolymers, may be used to form various cosmetic compositions, such as face masks, pore strips, and epilatories. Such compositions may provide an advantageous range of tensile, adhesion, and textural properties. The resulting properties may then be used to produce cosmetic compositions having improved adhesion, exfoliation, active delivery, longevity, or other desirable properties. For example, compositions disclosed herein may advantageously be drip-free, provide desired adhesive properties, and may peel in one piece. Embodiments disclosed herein may also provide for the ability to tailor the mechanical properties of a mask composition, advantageously allowing a cosmetic composition manufacturer or polymer supplier to determine copolymer and cosmetic composition components that meet customer demands for new and improved products.

While the disclosure includes a limited number of embodiments, those skilled in the art, having benefit of this disclosure, will appreciate that other embodiments may be devised which do not depart from the scope of the present disclosure. Accordingly, the scope should be limited only by the attached claims.

What is claimed:

1. An epilatory composition, comprising:
    40 to 80 wt % water;
    5 to 30 wt % of a mixture of at least one polyvinyl alcohol and at least one polyvinyl alcohol copolymer, wherein the at least one polyvinyl alcohol copolymer comprises a vinyl alcohol—vinyl amine copolymer having from greater than 0 to less than 20 wt % vinyl amine comonomer;
    1 to 15 wt % plasticizer, wherein the plasticizer is a linear or branched composition having from 3 to 15 wt % OH; and
    up to 40 wt % of one or more additives.

2. The epilatory composition of claim 1, wherein the plasticizer comprises a polyethylene glycol.

3. The epilatory composition of claim 1, wherein the composition is characterized in that it is removable from skin in essentially one piece.

4. The epilatory composition of claim 1, wherein the composition has a viscosity of greater than about 20000 cP, a Brookfield yield value of at least 5, and an adhesion to glass of at least 500 g.

5. The epilatory composition of claim 4, wherein the composition has an adhesion to glass in the range from about 500 to about 1000 g.

6. The epilatory composition of claim 4, wherein the composition has a drying time of less than 15 minutes.

7. The epilatory composition of claim 4, wherein the composition, upon drying, has a tensile strength to modulus ratio of at least 0.5.

8. The epilatory composition of claim 1, wherein the composition has a pH in the range from about 5.5 to about 7.5.

9. A cosmetic composition useful in pore strip, keratonic plug, and other cosmetic applications, comprising:
    40 to 80 wt % water;
    5 to 30 wt % of a mixture of at least one polyvinyl alcohol and at least one polyvinyl alcohol copolymer, wherein the at least one polyvinyl alcohol copolymer comprises a vinyl alcohol—vinyl amine copolymer having from greater than 0 to less than 20 wt % vinyl amine comonomer;
    1 to 15 wt % plasticizer, wherein the plasticizer is a linear, cyclic, or branched composition having greater than 25 wt % OH; and
    up to 40 wt % of one or more additives.

10. The composition of claim 9, wherein the plasticizer comprises at least one of glycerin, propylene glycol, butylene glycol, and dextrose.

11. The composition of claim 9, wherein the composition is characterized in that it is removable from skin in essentially one piece.

12. The composition of claim 9, wherein the composition has a viscosity of greater than about 20000 cP, a Brookfield yield value of at least 5, and an adhesion to glass of at least 150 g.

13. The composition of claim 12, wherein the composition has an adhesion to glass in the range from about 125 to about 350 g.

14. The composition of claim 12, wherein the composition has a drying time of less than 15 minutes.

15. The composition of claim 12, wherein the composition, upon drying, has a tensile strength to modulus ratio of at least 0.5.

16. The composition of claim 9, wherein the composition has a pH in the range from about 5.5 to about 7.5.

17. A method of preparing a cosmetic composition, the method comprising forming a mixture comprising the cosmetic composition of claim 1.

18. A method of preparing a cosmetic composition, the method comprising forming a mixture comprising the cosmetic composition of claim 9.

* * * * *